United States Patent [19]
Pachuk et al.

[11] Patent Number: 6,080,851
[45] Date of Patent: Jun. 27, 2000

[54] RIBOZYMES WITH LINKED ANCHOR SEQUENCES

[75] Inventors: Catherine J. Pachuk, Lansdowne; Leslie R. Coney, Rosemont; Fred T. Oakes, Malvern, all of Pa.

[73] Assignee: American Home Products Corporation, Madison, N.J.

[21] Appl. No.: 08/448,446

[22] PCT Filed: Nov. 16, 1993

[86] PCT No.: PCT/US93/11144

§ 371 Date: Jul. 10, 1995

§ 102(e) Date: Jul. 10, 1995

[87] PCT Pub. No.: WO94/13793

PCT Pub. Date: Jun. 23, 1994

Related U.S. Application Data

[63] Continuation-in-part of application No. 07/989,852, Dec. 4, 1992, Pat. No. 5,336,980.

[51] Int. Cl.⁷ .............................. C12Q 1/68; C07H 21/04
[52] U.S. Cl. ...................... 536/24.5; 536/23.1; 536/23.2; 536/24.31; 536/24.33; 435/6; 435/91.31; 435/375
[58] Field of Search ........................... 435/6, 91.1, 91.31, 435/172.1, 172.3, 320.1, 240.1, 240.2; 536/23.1, 23.2, 24.5, 24.33, 24.31; 514/44

[56] References Cited

U.S. PATENT DOCUMENTS

| | | | |
|---|---|---|---|
| 4,469,863 | 9/1984 | Ts'o et al. | 536/24.5 |
| 4,914,210 | 4/1990 | Levenson et al. | 548/413 |
| 4,987,071 | 1/1991 | Cech et al. | 435/91.31 |
| 5,037,746 | 8/1991 | Cech et al. | 435/91.31 |
| 5,612,469 | 3/1997 | Goodchild et al. | 536/23.1 |
| 5,714,383 | 2/1998 | Thompson et al. | 435/366 |

FOREIGN PATENT DOCUMENTS

| | | |
|---|---|---|
| 0421376 | 4/1990 | European Pat. Off. . |
| WO 88/04300 | 6/1988 | WIPO . |
| WO 89/05852 | 6/1989 | WIPO . |
| WO 90/06934 | 6/1990 | WIPO . |
| WO 91/03260 | 3/1991 | WIPO . |
| WO 91/14699 | 3/1991 | WIPO . |
| WO 91/06302 | 5/1991 | WIPO . |
| WO 91/12323 | 8/1991 | WIPO . |
| WO 91/18624 | 12/1991 | WIPO . |
| WO 91/18625 | 12/1991 | WIPO . |
| WO 91/18913 | 12/1991 | WIPO . |
| 9200080 | 1/1992 | WIPO . |
| WO 92/00080 | 1/1992 | WIPO . |
| WO 92/01806 | 2/1992 | WIPO . |
| 9303141 | 2/1993 | WIPO . |

OTHER PUBLICATIONS

Arad et al., "Use of Reconstituted Sendai Virus Envelopes for Fusion–mediated Microinjection of Double–stranded RNA: Inhibition of Protein Synthesis in Interferon–treated Cells", *Biochem. Biophys. Acta* 1986 859, 88–94.

Beaucage, S. and Caruthers, "Deoxynucleoside Phosphoramidites—a New Class of Key Intermediates for Deoxypolynucleotide Synthesis", *Tetrahedron Letters* 1981, 22, 1859–1862.

Fedor, M. and Uhlenbeck, "Kinetics of Intermolecular Cleavage by Hammerhead Ribozymes", *Biochemistry* 1992, 31, 12042–12054.

Boyer, H.W. and Roulland–Dussoix, "A Complementation Analysis of the Restriction and Modification of DNA in *Escherichia coli*", *J. Mol. Biol.* 1969, 41, 459–472.

Boyer, P.D., "The Enzymes", Student Ed., Academic Press, New York, NY, 1970.

Branch, A. and Robertson, "Efficient Trans Cleavage and a Common Structural Motif for the Ribozymes of the Human Hepatitis σ Agent", *PNAS USA* 1991, 88, 10163–10167.

Cech, T. and Bass, "Biological Catalysis by RNA", *Ann. Rev. Biochem.* 1986, 55, 599–629.

Celander, D. and Cech, "Visualizing the Higher Order Folding of a Catalytic RNA Molecule", *Science* 1991, 251, 401–407.

DeMonte et al., "Gene Transfer by Retrovirus–derived Shuttle Vectors in the Generation of Murine Bispecific Monoclonal Antibodies", *PNAS USA* 1990, 87, 2941–2945.

Drivas et al., "Ribozyme Cleavage of Chromosome Translocation–caused Fusion RNAs Associated with Certain Leukemias", 3rd International Symposium on Catalytic RNAs, San Diego, CA, Dec. 6–11, 1992, Abstract.

Edgington, "Ribozymes: Stop Making Sense", *Biotechnology* 1992, 10, 256–262.

Fedor, M.J. and Uhlenbeck, "Substrate Sequence Effects on 'Hammerhead' RNA Catalytic Efficiency", *PNAS USA* 1990, 87, 1668–1672.

Gait, M.J. ed., "Oligonucleotide Synthesis", IRL Press, Oxford, 1984.

Goodchild, "Enhancement of Ribozyme Catalytic Activity by a Contiguous Oligodeoxynucleotide (facilitator) and by 2'-O-methylation", *Nucleic Acids Research* 1992, 20(17), 4607–4612.

(List continued on next page.)

*Primary Examiner*—John L. LeGuyader
*Attorney, Agent, or Firm*—Howson and Howson

[57] ABSTRACT

Ribozymes are provided in which the ribozymes have a catalytic sequence, two legs and at least one anchor sequence complementary to the substrate mRNA at a location noncontiguous with the portions of the substrate mRNA complementary to the legs. In certain preferred embodiments, ribozymes capable of cleaving the L6 mRNA or both the L6 and K28 mRNAs are provided. Methods are provided for the treatment of chronic myelogenous leukemia (CML) and acute lymphoblastic leukemia (ALL) patients having the L6 and K28 translocations and, therefore, the L6 mRNA. Additionally, combination treatments comprising components specific for both the K28 and L6 mRNAs are provided. Combination treatments are also provided for those patients which express c-myc in combination with K28 and/or L6 mRNAs. Methods of treatment include, for example, administration of ribozymes and antisense oligonucleotides directed against these mRNAs.

31 Claims, 9 Drawing Sheets

OTHER PUBLICATIONS

Goodchild and Kohli, "Ribozymes that Cleave an RNA Sequence form Human Immunodeficiency Virus: The Effect of Flanking sequence on Rate", *Archives of Biochemistry and Biophysics* 1991, 284, 386–391.

Groffen, J. et al., "Philadelphia Chromosomal Breakpoints ar Clustered within a Limited Region, bcr, on Chromosome 22", *Cell* 1984, 36, 93–99.

Guo, J. et al., "Detection of BCR–AB1 Proteins in Blood Cells of Benign Phase Chronic Myelogenous Leukemia Patients", *Cancer Research* 1991, 51, 3048–3051.

Hantzopoulos et al., "Improved Gene Expression Upon Transfer of the Adenosine Deaminase Minigene Outside the Transcriptional Unit of a Retroviral Vector", *PNAS USA* 1989, 86, 3519–3523.

Haseloff, "Simple RNA Enzymes with New and Highly Specific Endoribonuclease Activities", *Nature* 1988, 334, 585–591.

Heisterkamp et al., "Structural Organization of the bcr Gene and its Role in the Ph' Translocation", *Nature* 1985, 315, 758–761.

Heisterkamp, N. et al., "Localization of the c–abl Oncogene Adjacent to a Translocation Break Point in Chronic Myelocitic Leukemia", *Nature* 1983, 306, 239–242.

Hermans, A. et al., "Absence of Alternative Splicing in bcr–abl mRNA in Chronic Myeloid Leukemia Cell Lines", *Blood* 1988, 72, 2066–2069.

Herschlag, D., "Implications of Ribozyme Kinetics for Targeting the Cleavage of Specific RNA Molecules in vivo: More isn't Always Better", *PNAS USA* 1991, 88, 6921–6925.

Herschlag, D. and Cech, "Catalysis of RNA Cleavage by the *Tetrahymena thermophila* Ribozyme. 2. Kinetic Description of the Reaction of an RNA Substrate That Forms a Mismatch at the Active Site", *Biochem.* 1990, 29, 10172–10180.

Innis et al., *PCR Protocols*, A Guide to Methods and Applications, 1990.

Kashani–Sabet et al., "Reversal of the Malignant Phenotype by an Anti–ras Ribozyme", *Antisense Res. and Dev.* 1992, 2, 3–15.

Kikuchi, Y. and Sasaki, "Site–specific Cleavage of Natural mRNA Sequences by Newly Designed Hairpin Catalytic RNAs", *Nucleic Acids Res.* 1991, 24, 6751–6755.

Konopka, J. et al., "Cell Lines and Clinical Isolates derived from Ph[1]–Positive Chronic Myelogenous Leukemia Patients Express c–abl Proteins with a Common Structural Alteration", *PNAS USA* 1985, 82, 1810–1814.

Kubonishi, I. and Miyoshi, "Establishment of a Ph[1] Chromosome–Positive cell Line form Chronic Myelogenous Leukemia in Blast Crisis", *Int. J. Cell Cloning* 1983, 1, 105–117.

Lange et al, "Site–Specific Cleavage of BCR/ABL mRNA by Synthetic Ribozymes—In Vitro and In Vivo Effects", 3rd International Symposium on Catalytic RNAs, San Diego, CA, Dec. 6–11, 1992. Abstract.

Lange, W. et al., "Detection by Enzymatic Amplification of bcr–abl mRNA in Peripheral Blood and Bone Marrow Cells of Patients with Chronic Myelogenous Leukemia", *Blood* 1989, 73, 1735–1741.

Leamon and Low, "Delivery of Macromolecules into Living Cells: A Method that Exploits Folate Receptor Endocytosis", *PNAS USA* 1991, 88, 5572–5576.

Lozzio et al., "Human Chronic Myelogenous Leukemia Cell–Line With Positive Philadelphia Chromosome", *Blood* 1975, 45, 321–334.

McLaughlin et al., "In vitro Transformation of Immature Hematopoietic Cells by the P210 BCR/ACL Oncogene Product of the Philadelphia Chromosome", *PNAS USA* 1987, 84, 6558–6562.

Mercola, M. et al., "Transcriptional Enhancer Elements in the Mouse Immunoglobulin Heavy Chain Locus", *Science* 1993, 221, 663–665.

Mills, K.I. et al., "The Site of the Breakpoint Within the bcr is a Prognostic Factor in Philadelphia–Positive CML Patients", *Blood* 1988, 72, 1237–1241.

Nakamura, D. and Inouye, "DNA Sequence of the Gene for the Outer Membrane Lipoprotein of E. coli: an Extremely AT–Rich Promotoer", *Cell* 1979, 18, 1109–1117.

Nowell, P.C. and Hungerford, "A Minute Chromosome in Human Chronic Granulocytic Leukemia", *Science* 1960, 132, 1497.

Heus, H. et al., "Sequence–dependent Structural Variations of Hammerhead RNA Enzymes", *Nucleic Acids Research* 1990, 18, 1103–1108.

Paolella, G. et al., "Nuclease Resistant Ribozymes with High Catalytic Activity", *The EMBO J.* 1992, 1913–1919.

Perreault, J.–P. et al., "Mixed Deoxy– and Ribo–oligonucleotides with Catalytic Activity", *Nature* 1990, 344, 565–567.

Pyle, A. et al., "Direct Measurement of Oligonucleotide Substrate Binding to Wild–type and Mutant Ribozymes From Tetrahymena", *PNAS USA* 1990, 87, 8187–8191.

Rosenberg, S. et al., "Gene Transfer into Humans—Immunotherapy of Patients with Advanced Melanoma, Using Tumor–Infiltrating Lymphocytes Modified by Retroviral Gene Transduction", *New Eng. J. Med.* 1990, 570–578.

Roth, M.S. et al., "Detection of Philadelphia Chromosome–Positive Cells by the Polymerase Chain Reaction Following Bone Marrow Transplant for Chronic Myelogenous Leukemia", *Blood* 1989, 74, 882–885.

Roux, P. et al., "A Versatile and Potentially General Approach to the Targeting of Specific Cell Types by Retroviruses: Application to the Infection of Human Cells by Means of Major Histocompatibility Complex Class I and Class II Antigens by Mouse Ecotropic Murine Leukemia Virus–derived Viruses", *PNAS USA* 1989, 86, 9079–9083.

Rowley, J., "Identification of the Constant Chromosome Regions Involved in Human Hematologic Malignant Disease", *Science* 1982, 216, 749–751.

Rowley, J., "A New Consistent Chromosomal Abnormality in Chronic Myelogenous Leukaemia Identified by Quinacrine Fluorescence and Giemsa Staining", *Nature* 1973, 243, 290–293.

Ruffner, D. et al., "Sequence Requirements of the Hammerhead RNA Self–Cleavage Reaction", *Biochemistry* 1990, 29, 10695–10702.

Sambrook, J., Fritsch and Maniatis, "Molecular Cloning, a Laboratory Manual", Cold Spring Harbor, NY, Cold Spring Harbor Laboratory, 1989.

Sawyers, C. et al., "Dominant Negative MYC Blocks Transformation by ABL Oncogenes", *Cell* 1992, 70, 901–910.

Sawyers, C. et al., "Molecular Relapse in Chronic Myelogenous Leukemia Patients After Bone Marrow Transplantation Detected by Polymerase Chain Reaction", *PNAS USA* 1990, 87, 563–567.

Schaefer–Rego, K. et al., "CML Patients in Blast Crisis Have Breakpoints Localized to a Specific Region of the BCR", *Blood* 1987, 70, 448–455.

Selleri, L. et al., "Chronic Myeloid Leukemia May Be Associated with Several bcr–abl Transcripts Including the Acute Lymphoid Leukemia–Type 7 kb Transcript", *Blood* 1990, 75, 1146–1153.

Shannon et al., "Simultaneous Expression of CML and all Types of mRNA Transcripts in Philadelphia (Ph[1]) Chromosome Positive Leukemia", Abstract 812.

Shtalrid, M. et al., "Analysis of Breakpoints Within the bcr Gene and Their Correlation With the Clinical Course of Philadelphia–Positive Chronic Myelogenous Leukemia", *Blood* 1988, 72, 485–490.

Shtivelman, E. et al., "Fused Transcript of abl and bcr Genes in Chronic Myelogenous Leukaemia", *Nature* 1985, 315, 550–554.

Shtivelman, E. et al., "Alternative Splicing of RNAs Transcribed from the Human abl Gene and from the bcr–abl Gene", *Cell* 1986, 47, 277–284.

Snyder et al., "Persistence of bcr–abl Gene Expression Following Bone Marrow Transplantation for Chronic Myelogenous Leukemia in Chronic Phase", *Transplantation* 1991, 51, 1033–1040.

Snyder et al, "Ribozyme–Mediated Inhibition of bcr–abl Gene Expression in a Philadelphia Chromosome–Positive Cell Line", 3rd International Symposium on Catalytic RNAs, San Diego, CA, Dec. 6–11, 1992, Abstract.

Wang, C.–Y. and Huang, "pH–sensitivie Immunoliposomes Mediate Target–cell–specific Delivery and Controlled Expression of a Foreign Gene in Mouse", *PNAS USA* 1987, 84, 7851–7855.

Young, B. et al., "Mutations in a Nonconserved Sequence of the Tetrahymena Ribozyme Increase Activity and Specificity", *Cell* 1991, 67, 1007–1019.

Anfossi et al., "An Oligomer Complementary to c–myb–encoded mRNA Inhibits Proliferation of Human Myeloid Leukemia Cell Lines", *PNAS USA* 1989, 86, 3379–3383.

Lasky et al., "Effects of 1alpha,25–DihydroxyvitaminD3 on the Human Chronic Myelogenous Leukemia Cell Line RWLeu–4", *Cancer Research* 1990, 50, 3087–3094.

M. Tabler et al, "Catalytic Antisense RNAs Produced by Incorporating Ribozyme Cassettes into cDNA", *Gene*, 108(2):175–183 (Dec. 15, 1991).

M. Koizumi et al, "Cleavage of Specific Sites of RNA by Designed Ribozymes", *FEBS Letters*, 239(2):285–288 (Nov., 1988).

Snyder et al. Blood. 82:600–605 (Jul. 1993).

Branch TIBS 23:45–50 1998.

Arivas et al. J. Cell. Biochem. Suppl. 0(17 Part E): p. 211 (1993).

Wright et al. Exp. Hematology 21:1714–1718 (1993).

Snyder et al. Blood 82 (10 Suppl. 1):p. 40A (1993).

Lange et al. Annals of Hematology 65(Suppl.): A7, No. 231 (1992).

Lange et al. Leukemia 7(11):1786–1794 (Nov., 1993).

Vaerman et al. Stem Cells 11(Suppl. 3):89–95 (1993).

Pachuk et al. Proceedings of the American Assoc. for Cancer Res. 34:388(1993).

Synder et al. Blood 78(Suppl. 1):330a, No. 1309 (1991).

Sokol et al. Transgenic Research 5:363–371 (1996).

Stull et al. Pharm. Res. 12: 465–487 (1995).

Coney et al. J. Cell. Biochem. 17 Suppl. E, S402, p. 211, 1993.

Arivas et al. J. Cell. Biochem. 17 Suppl. E, S402, p. 211, 1993.

K28 TRANSLOCATION

L6 TRANSLOCATION

CAAUAAGGAAG|AAGCCCUUCAGCGGGCCAGUAGCAUCUGACUU (SEQ ID NO:24)

BCR exon 2                    ABL exon 2

ACAGCAUUCCGCUGACCAUCAAUAAGGAAG | AAGCCCCUUCAGGGCCAGUAGCAUCUGACUU.... SUBSTRATE (SEQ ID NO:1)

L6(2)₀ (SEQ ID NO:3)   CCUUC   UUCGGGA  GUCGGCCG          RIBOZYME
L6(2)₂ (SEQ ID NO:4)   2.AC             A      C
L6(2)₃ (SEQ ID NO:5)   3.ACA            A      U
L6(2)₄ (SEQ ID NO:6)   4.ACAA           G      G
                                                 A
                              G^A GGAC_A G U
                              U_G CCUG   A G

*Fig. 3*

RIBOZYMES WITH LINKED ANCHOR SEQUENCES

This application is a 371 of International Patent Application PCT/US93/11144, filed Nov. 16, 1993, which is a continuation-in-part of application No. 07/989,852, filed Dec. 4, 1992, now abandoned.

FIELD OF THE INVENTION

The present invention provides ribozymes having an anchor sequence capable of anchoring the ribozyme to a region of the substrate mRNA that may be noncontiguous with the region of substrate mRNA complementary to a leg of the ribozyme. Certain preferred embodiments of the present invention include ribozymes capable of cleaving the L6fusion mRNA or both the L6 and K28 mRNAs expressed by the hematopoietic cells of some CML and ALL patients. The present invention also furnishes methods of treating leukemias using oligonucleotide therapeutics.

BACKGROUND OF THE INVENTION

The potential use of ribozymes as pharmaceuticals is an exciting prospect. An important requirement for the development of ribozyme pharmaceutical products is the ability to specifically target a ribozyme to a cellular RNA of interest. This can be especially difficult when designing a ribozyme for a chimeric RNA molecule that is homologous to a second RNA molecule, particularly if cleavage of the second RNA is detrimental to the host. It may be equally difficult to target an RNA molecule that is folded in a way that prevents ribozyme interactions at or near the ribozyme cleavage site. We have encountered both of these problems in our attempts to design ribozymes that are specific for an aberrant mRNA associated with chronic myelogenous leukemia (CML).

Chronic Myelogenous Leukemia (CML) and acute lymphocytic leukemia (ALL) represent two different types of leukemias. CML is a chronic myeloproliferation disorder associated with the cytogenic marker called the Philadelphia chromosome (Nowell, P. C. and Hungerford, D. A., *Science* 1960, 132, 1497) in approximately 95% of patients. The Philadelphia chromosome is a chromosomal abnormality resulting from reciprocal translocations between chromosomes 9 and 22 (Mercola, M. et al., *Science* 1933, 221, 663).

The breakpoints on chromosome 22 are clustered in a 6 Kb region termed the breakpoint cluster region (bcr) (Groffen, J. et al., *Cell* 1984, 36, 93–99), while on chromosome 9, the breakpoints are scattered throughout a 90 Kb region upstream from c-abl exon 2 (Heisterkamp, N. et al., *Nature* 1983, 306, 239–242). The resultant fusion transcripts, which are about 8.5 kb long, contain bcr sequences upstream and abl sequences downstream.

The cellular gene abl, a highly conserved gene, represents the progenitor of the viral transforming gene (v-abl) of Abelson leukemia virus. v-abl confers to Abelson leukemia virus the ability to transform a broad range of hematopoietic cell types. Transformation is mediated by a tyrosine kinase encoded by the viral genome, composed of v-abl polypeptide attached at its N-terminus to viral gag polypeptide. The human abl gene was mapped to chromosome 9, and is expressed as a 145 kd protein having tyrosine kinase activity. Misregulation of abl is implicated in CML in humans. Shtivelman et al., *Cell* 1986, 47, 277–284.

The various 9:22 translocations associated with the Philadelphia chromosome can be subdivided into two types: K28 translocations and L6 translocations. In the K28 mRNA, abl exon 2 is linked to bcr exon 3. In the L-6 mRNA, abl exon 2 is linked to bcr exon 2. C-myc mRNA is pertinent for blast crisis in CML.

A third type of 9:22 translocation has also been identified. The chromosome 9 breakpoints specific for this type of translocation are located 5' of the L6 breakpoints. The presence of this abnormal chromosome, however, is associated with the establishment of acute lymphocytic leukemia (ALL) not CML. Selleri et al., *Blood* 1990, 75, 1146–1153. Further, the K28 and L6 mRNAs have been associated with some patients with ALL.

Much emphasis has been placed on the role of mRNA K28 and the establishment of CML. (Shtivelman, E. et al., *Cell* 1986, 47, 277–284; Kubonishi, I. and Miyoshi, I., Int. J. Cell Cloning 1983, 1, 105–117; Shtalrid, M. T. et al., *Blood* 1988, 72, 485–490; Mills, K. I. et al., *Blood* 1988, 72, 1237–1241).

In the K28 translocations, the chromosomal 22 breakpoints lie between bcr exons 3 and 4 (Shtivelman, E. et al., *Cell* 1986, 47, 277–284). Transcription through this region yields an mRNA which can be alternatively spliced to yield two distinct mRNAs (Shtivelman, E. et al., *Cell* 1986, 47, 277–284): mRNA K28 and mRNA L6. In mRNA K28, bcr exon 3 is fused to abl exon 2, while in mRNA L6, bcr exon 2 is fused to abl exon 2. Importantly, the mRNA yielded can change during the course of disease. In the L6 translocations, the chromosomal breakpoints lie between bcr exons 2 and 3 (Shtivelman, E. et al., *Cell* 1986, 47, 277–284). Transcription through this region yields only one species of mRNA, mRNA L6. The K28 and the L6 mRNAs encode a protein with an aberrant tyrosine kinase activity which is unique to CML cells and which is believed to play a key role in the establishment of CML. McLaughlin et al., *Proc. Nat'l. Acad. Sci.* 1987, 84, 6558–6562.

To date, bone marrow transplantation has been the most effective way to treat CML. Nonetheless, using a more sensitive technique, it has been demonstrated that in some patients receiving ablative radiation and/or chemotherapy followed by bone marrow transplantation, residual leukemia cells may persist. Researchers have detected residual bcr-abl mRNA in patients following bone marrow transplantation in a study using a more sensitive PCR assay. Snyder et al., *Transplantation* 1991, 51, 1033–1040. There remains an unmet need in reducing the level of mRNAs and their protein products implicated in leukemias in the treatment of CML and ALL. These mRNAs include the bcr-abl transcripts such as the K28 and L6 mRNAs, as well as c-myc mRNA.

Ribozymes offer an attractive alternative. Chimeric RNAs, such as those occurring in CML, can be ideal candidates for ribozyme targeting particularly when a ribozyme cleavage site is located within 2 or 3 nucleotides of the chimeric junction, i.e. near the junction. In this case a ribozyme can be targeted specifically to the chimeric molecule but not the non-chimeric molecule by specifying that 1) ribozyme sequences 5' of the catalytic region be complementary to chimeric RNA sequences located immediately 3' of the cleavage site, and 2) ribozyme sequences 3' of the catalytic region be complementary to chimeric sequences immediately 5' of the cleavage site. The specificity of the ribozyme is thus, presumably, maintained and the potentially harmful results of non-specific ribozyme cleavage can be avoided.

However, not all chimeric mRNAs exhibit a convenient site for ribozyme cleavage so near to the junction site. Examination of the L6 bcr-abl mRNA sequence reveals that the closest "NUX" ribozyme cleavage sites in the vicinity of the bcr-abl junction are located 7, 8, and 19 nucleotides away from the junction (see FIG. 1b). It is not feasible to target any of these sites for ribozyme cleavage in the manner described because such ribozymes would likely also cleave normal abl mRNA or normal bcr mRNA. In addition, computer predictions for the secondary structures of L6 bcr-abl mRNA suggest that these sites may be inaccessible to conventional ribozymes. Accordingly, we initiated new approaches to the design of ribozymes specific for L6 bcr-abl mRNA.

Reddy, et al., WO 92/00080, published Jan. 9, 1992, report a ribozyme capable of cleaving the hybrid bcr-abl "gene" of CML at or near the breakpoint. The translocation product targeted was not specified, and the implication was that only one translocation occurred. Nevertheless, from sequence complementarity, it appears that the ribozyme of Reddy was directed against the K28 translocation. This translocation exhibits a convenient site near the junction for conventional ribozyme cleavage. Tests verifying specificity of the ribozyme for hybrid bcr-abl were not provided.

As noted previously, the particular message transcribed by K28 can change during the course of disease. Further, certain CML patients express the L6 mRNA either alone or in addition to the K28 mRNA. Shtivelman et al., *Cell* 1986, 47, 277–284. There remains an unsolved problem which has not been addressed; the L6 mRNA. The L6 mRNA will most likely be unaffected by treatments designed solely to target the K28 mRNA. Further, there is an unmet need in targeting the c-myc mRNA in conjunction with the bcr-abl transcripts.

The present invention provides oligonucleotide therapeutics and methods of treating CML and ALL whereby the aforementioned transcripts are specifically targeted. The present invention also provides ribozymes capable of cleaving L6 mRNA, or both L6 and K28 mRNA.

The present invention also addresses, in general, an unmet need for ribozymes capable of cleaving a target mRNA in which the catalytic recognition sequence is located at a distance from the nucleation site, the junction of a chimeric target mRNA, or in which catalytic recognition sequences are not readily accessible due to secondary structure. The ribozymes of the present invention are useful, for example, in the treatment of diseases involving translocations, such as CML, ALL and follicular lymphoma.

SUMMARY OF THE INVENTION

We have developed a generic approach for ribozyme targeting using a bcr-abl fusion mRNA associated with the establishment of chronic myelogenous leukemia (CML) as a model. Using this approach, we successfully directed ribozyme nucleation to a site on a bcr-abl RNA substrate that is distant from the cleavage site. Generally, the nucleation sites are immediately contiguous to the cleavage site and the legs of the ribozyme can perform the nucleation, i.e., initial contact with the substrate facilitating subsequent hybridization, twisting, and cleavage. However, sometimes, there are no sites immediately contiguous to the cleavage site available for nucleation. With the ribozymes of the invention, non-contiguous regions of the substrate RNA can therefore be utilized for the separate events of ribozyme nucleation and ribozyme cleavage. This approach has led to the development of a series of ribozymes specific for the L6 and K28 bcr-abl fusion mRNAs. These ribozymes were targeted to the L6 bcr-abl RNA via an anchor sequence complementary to the bcr sequence that is proximal to the bcr-abl junction. Cleavage by these ribozymes occurred at a downstream site located within an abl specific sequence in the fusion mRNAs. Normal abl and bcr substrate RNAs were not cleaved. The approach of our invention has made it possible to increase the specificity of ribozyme cleavage for a chimeric RNA. In addition, this same approach allows a ribozyme to cleave at a site that is otherwise inaccessible due to the secondary structure of the substrate RNA or, in the case of chimeric RNA, at a site distant from the junction.

This invention provides ribozymes capable of cleaving an L6 mRNA having bcr exon 2 sequences fused at a junction to abl exon 2 sequences. These ribozymes comprise nucleotides or derivatives thereof having at least one region complementary to abl exon 2 and at least one catalytic sequence capable of cleaving abl or bcr sequences. The ribozymes further comprise at least one region complementary to bcr exon 2. In addition, ribozymes are provided which are capable of cleaving at a distance from at least one region of complementarity to the substrate mRNA.

The present invention also provides ribozymes having an anchor sequence for anchoring the ribozyme to a region of the substrate mRNA that may be noncontiguous with the region of substrate mRNA complementary to a leg of the ribozyme. Certain preferred embodiments provide ribozymes capable of cleaving a target mRNA in which the catalytic recognition sequence is located at a distance from the region in the target mRNA that is complementary to the anchor of the ribozyme. The ribozymes of the present invention are useful, for example, in the treatment of diseases involving translocations, such as CML, ALL and follicular lymphoma. The ribozymes of the present invention are also useful, for example, to cleave mRNAs associated with diseases in which the mRNA has an area causing a steric obstacle to binding of the ribozyme to the substrate near the catalytic recognition site.

Methods are provided for treating vertebrates with chronic myelogenous leukemia (CML) and acute lymphoblastic leukemia (ALL) in which the L6 mRNA or both the L6 and K28 mRNAs are expressed. These methods comprise administering at least one oligonucleotide therapeutic, such as a ribozyme or an antisense oligonucleotide, capable of decreasing expression of L6 mRNA or both the L6 and K28 mRNAs.

Combination treatments are preferred embodiments wherein when both the L6 mRNA and the K28 mRNA are targeted. For example, an L6-specific ribozyme is used in conjunction with a ribozyme specific for the K28 transcript in those patients who express both types of mRNAs. Combination therapy is especially important to those patients having the K28 translocation who express both the L6 and K28 mRNAs either simultaneously or consecutively during the course of the disease. Treatment with a therapeutic agent specific for either the L6 or the K28 mRNA would likely be ineffective in these patients, unless the ribozyme was capable of cleaving both.

Unexpectedly, it was discovered that the ribozymes according to the invention, directed against the L6 mRNAs, also cleaved the K28 substrate RNAs, but not the substrates representing native abl and bcr. This finding was particularly surprising because the K28 translocation contains a 75 base-pair exon which is not present in the L6 translocation. The ribozymes according to the invention were able to nucleate and cleave the K28 substrate without sacrificing specificity. This is, to the inventors' knowledge, the first report of a single ribozyme specific for two aberrant translocation products. Thus, combination therapy can be effected by the administration of a single ribozyme.

Further, combination treatments are provided for those patients also expressing c-myc using oligonucleotide therapeutics (such as antisense oligonucleotides or ribozymes)

specific for c-myc RNA along with oligonucleotide therapeutics specific for at least one of the K28 and L6 mRNAs.

BRIEF DESCRIPTION OF THE DRAWINGS

FIG. 3 illustrates certain preferred embodiments of the L6(2) ribozymes of the present invention described in Example 2.

DETAILED DESCRIPTION OF THE INVENTION

Figure 1A:
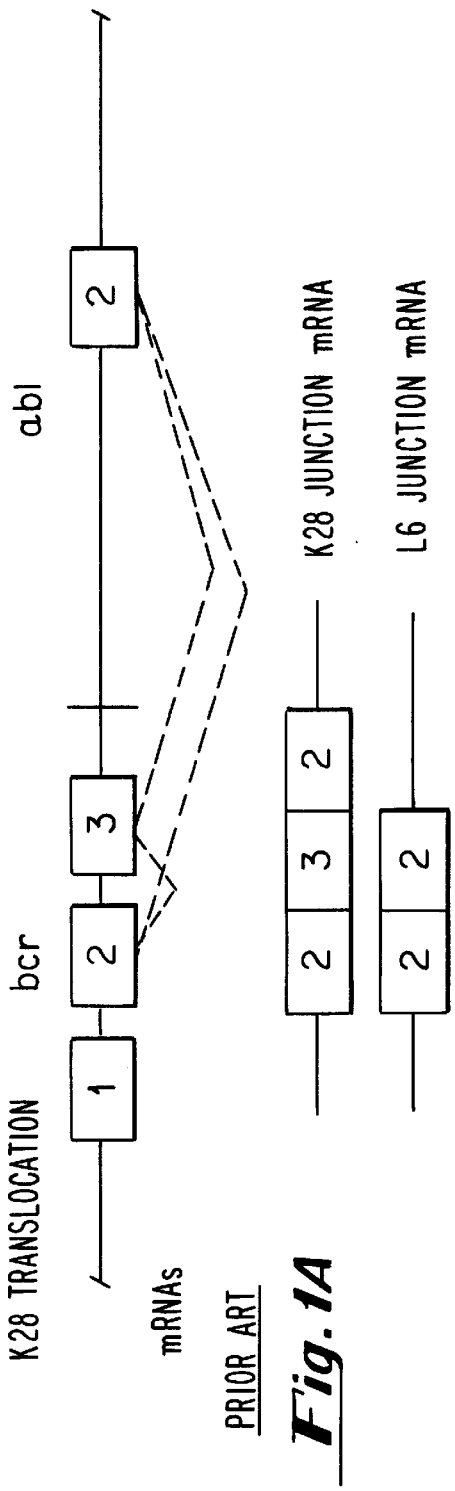
FIGS. 1A–1B depicts the K28 and L6 translocations.

In one aspect, the present invention provides ribozymes having an anchor sequence for anchoring the ribozyme to a region of the substrate mRNA that may be noncontiguous with the region of substrate mRNA complementary to a leg of the ribozyme. Ribozymes capable of cleaving a sequence that is present at a distance from the region of nucleation are provided as embodiments of the invention. Certain preferred embodiments include ribozymes capable of cleaving an L6 mRNA. The invention also furnishes methods of treating a vertebrate suspected of having CML or ALL in which the vertebrate's hematopoietic cells are believed to express L6 mRNA. Methods of treatment comprise administering to the vertebrate at least one oligonucleotide therapeutic targeted to the L6 mRNA. Other methods also target c-myc in conjunction with at least one of L6 and K28 mRNAs.

One embodiment of the present invention involves ribozymes effective for cleaving the L6 mRNA within either abl or bcr sequences and preferably within abl, which sequences are present in both the K28 and the L6 mRNAs.

Ribozymes are catalytic RNAs which are capable of self-cleavage or cleavage of another RNA molecule. Several different types of ribozymes, such as hammerhead, hairpin, Tetrahymena group I intron, axhead, and RNase P are known in the art. (S. Edgington, *Biotechnology* 1992 10, 256–262.) Hammerhead ribozymes have a catalytic site which has been mapped to a core of less than 40 nucleotides. Several ribozymes in plant viroids and satellite RNAs share a common secondary structure and certain conserved nucleotides. Although these ribozymes naturally serve as their own substrate, the enzyme domain can be targeted to another RNA substrate through base-pairing with sequences flanking the conserved cleavage site. This ability to custom design ribozymes has allowed them to be used for sequence-specific RNA cleavage. (G. Paolella et al., *EMBO* 1992, 1913–1919.) It will therefore be within the scope of one skilled in the art to use different catalytic sequences from various types of ribozymes, such as the hammerhead catalytic sequence and design them in the manner disclosed herein.

Ribozymes may also be designed to enhance the rate of the cleavage reaction. For example, Goodchild and Kohli, *Archives of Biochemistry and Biophysics* 1991, 284, 386–391 teach the reduction of complementary nucleotides capable of base pairing with the substrate from 20 to 12. Additionally, mismatches may be introduced to allow recognition to be spread over a larger number of bases while preventing binding that is too strong. For a discussion of kinetics, see for example, Herschlag, *Proc. Natl. Acad. Sci.* 1991, 88, 6921–6925. Certain preferred embodiments of the invention include sufficient complementarity to specifically target the abl-bcr fusion transcript while maintaining efficiency of the cleavage reaction.

An example of an assay for determining whether the ribozyme is capable of cleaving the targeted mRNA is as follows. An RNA substrate, such as the bcr-abl substrate, is incubated with the ribozyme to be tested under appropriate conditions. The reaction products are then tested using, for example, gel electrophoresis. A detectable cleavage of the substrate mRNA represents a positive result indicating the ribozyme is capable of cleaving the target mRNA.

A preferred embodiment of the invention provides ribozymes comprising at least one region complementary to abl, and a region complementary to bcr. Further preferred embodiments include a spacer region of non-complementarity between a region of complementarity (such as an anchor) and a second region of complementarity (such as a leg). Preferably, the ribozyme catalytic motif is the hammerhead catalytic core sequence, and more preferably, the catalytic sequence is

5' CUGAUGAGUCCGUGAGGACGAA 3' (SEQ ID NO: 11).

Preferred embodiments have two legs having about 2 to about 30 nucleotides, and preferably about 15 nucleotides, complementary to abl sequences. The lengths of the legs do not have to be the same. Preferred embodiments also include about 2 to about 500, preferably about 11, nucleotides complementary to the bcr sequences, and representing an anchor. The ribozymes of the present invention are capable of cleaving L6 and/or K28 mRNAs.

Further preferred embodiments include about 1 to about 3,000, preferably about 1 to about 1,000, more preferably about 1 to about 100, and most preferably about 13, nucleotides of non-complementary spacer sequence between the complementary regions, such as the region complementary to abl and the region complementary to bcr. Certain preferred embodiments cleave the bcr-abl fusion mRNA at the GUA site within the abl region located 19 nucleotides 3' of the bcr-abl junction. These are designated as the L6(1) class of ribozymes in the discussion which follows. Other preferred embodiments target the CUU site within the abl region located 7 nucleotides 3' of the bcr-abl junction, and these are designated as the L6(2) class. Given the present disclosure, one skilled in the art would recognize these and other sequences of potential cleavage sites, depending upon the targeted sequence and the type of catalytic core motif used in the ribozyme.

Figure 2:
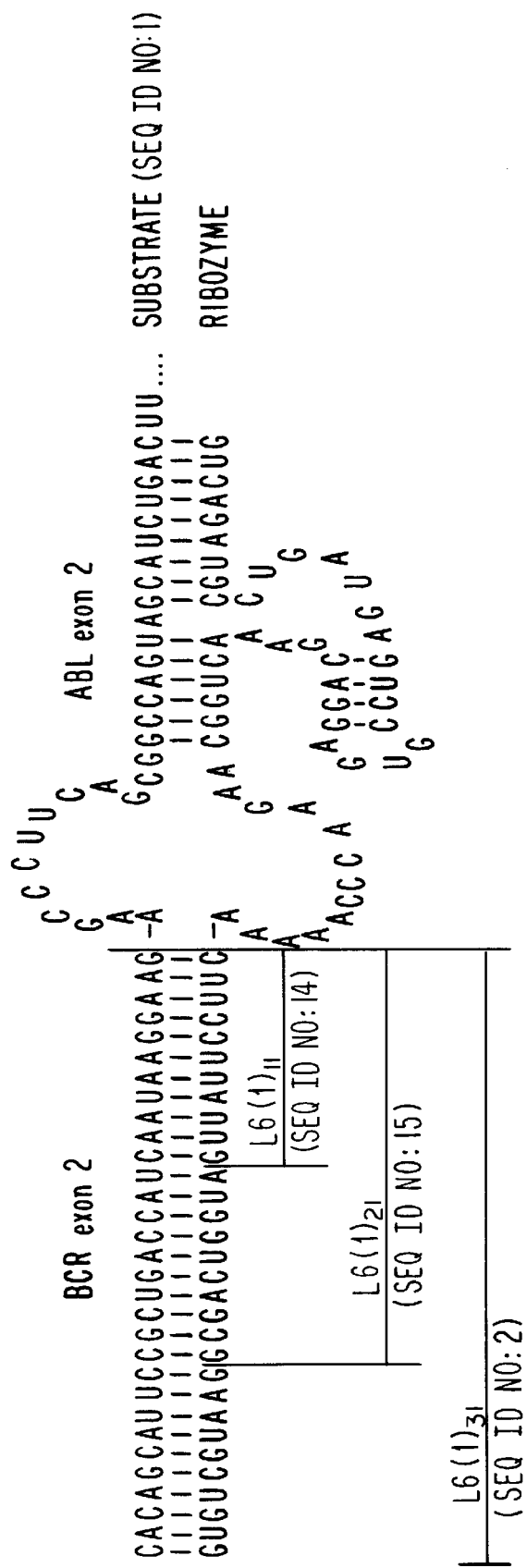
FIG. 2 depicts certain preferred embodiments of the L6(1) ribozymes of the present invention described in Example 1.

The L6(1) class of ribozymes were designed to cleave at the GUA motif located 19 nucleotides (nts) 3' of the bcr-abl junction (FIG. 2). These ribozymes contain sequences that are complementary to abl sequences present on either side of the GUA triplet and in addition contain an anchor sequence that is complementary to sequences in bcr exon 2 which are non-contiguous with the sequences complementary to abl. FIG. 2, and subsequent figures, simplified representations of the associations immediately prior to cleavage for illustration purposes. As is evident from the predicted secondary structure depicted in FIGS. 6a and 6b, the substrate immediately 3' of the junction is not readily available for complementary base-pairing.

Figure 6A:
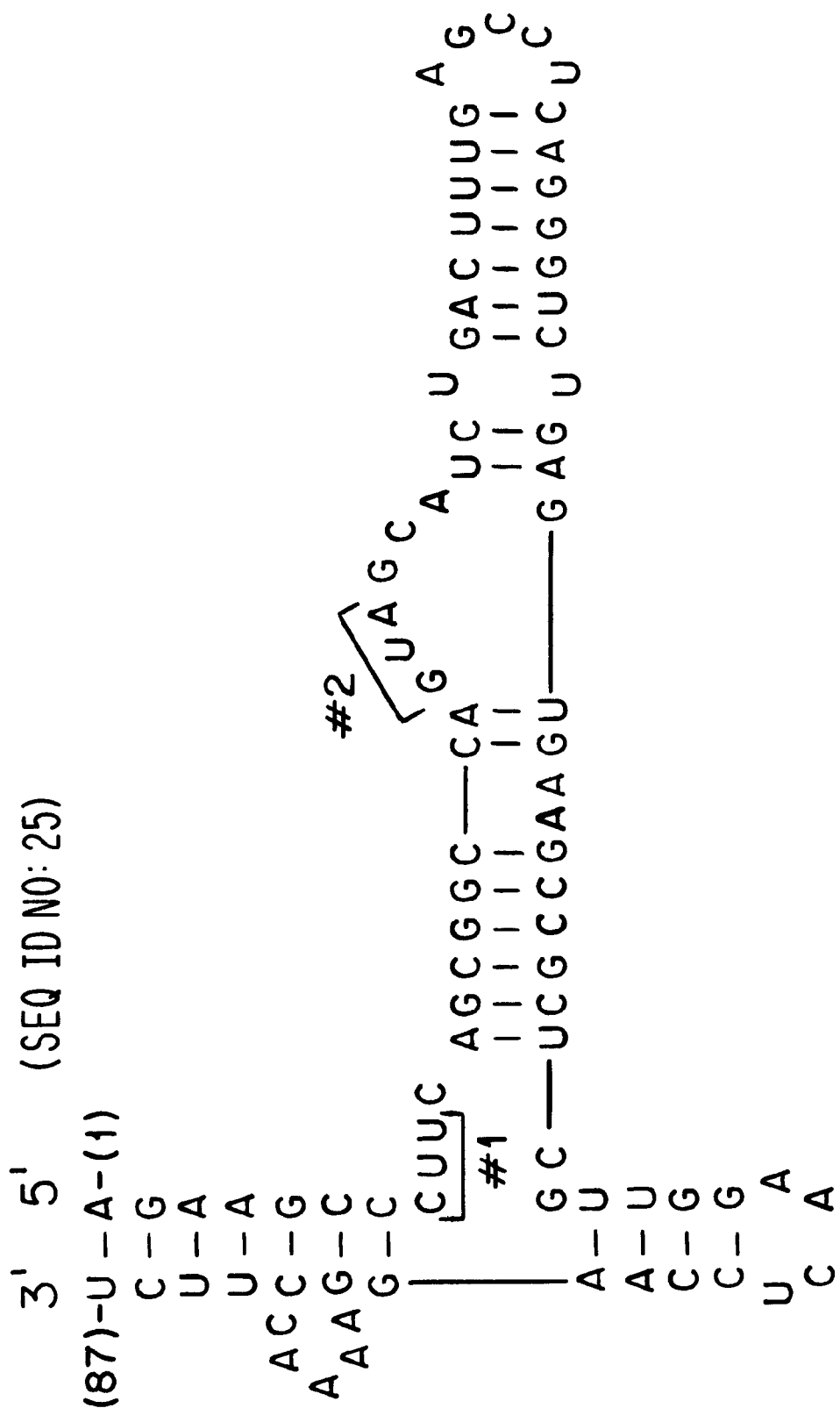
FIGS. 6 a and b illustrate the proposed secondary structure in the substrate RNAs.
Figure 6B:
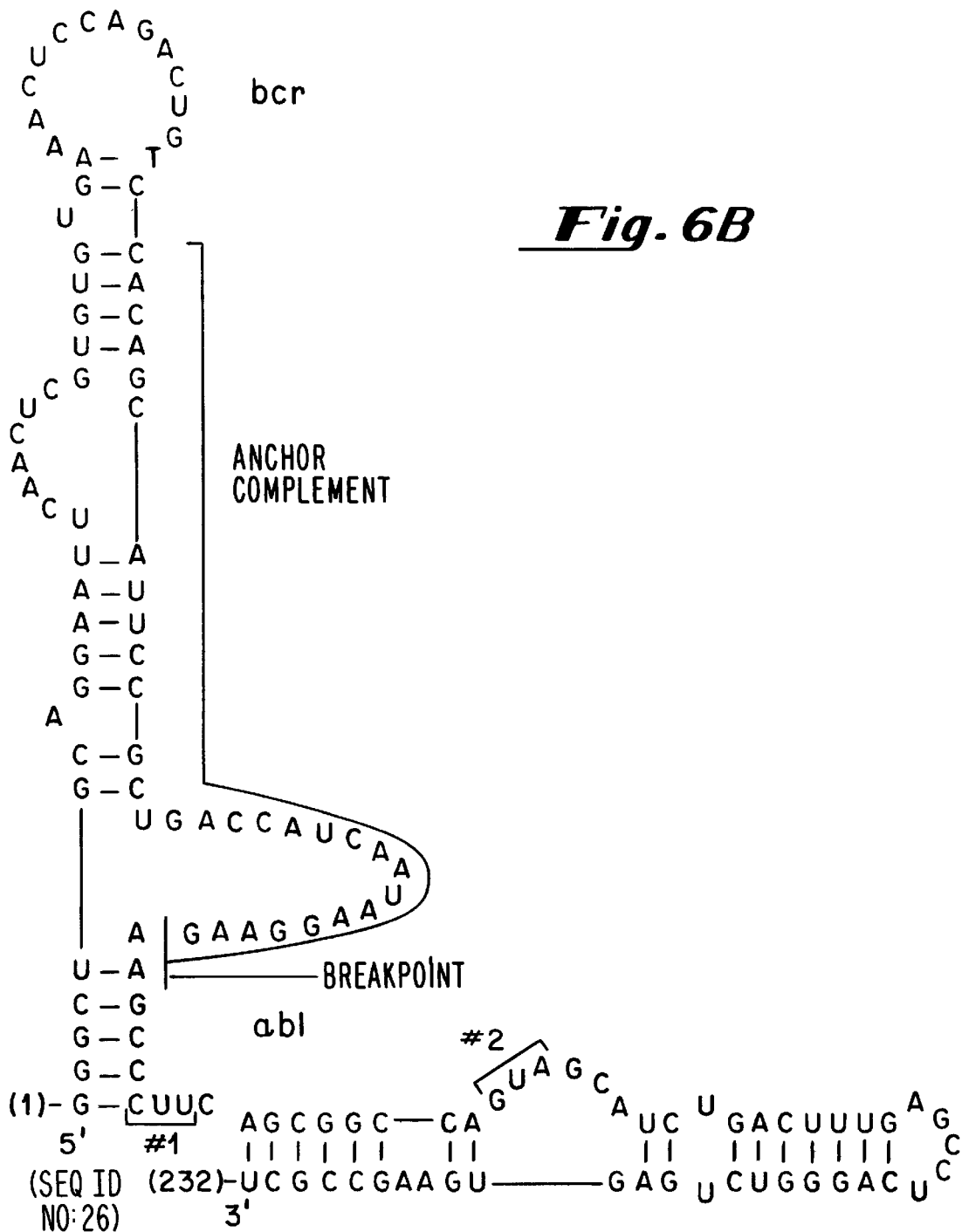

Secondary structure predictions for substrate RNAs were generated using the Zucker and Steigler algorithm for RNA folding. Although the complete nucleotide sequence of the synthetic substrate molecules was analyzed, only a portion of the folded structure is presented in the figures. The anchor complement and substrate cleavage sites are indicated. Designations #1 and #2 indicate the two ribozyme cleavage sites CUU and GUA, respectively. The bcr-abl junction in the L6 bcr-abl substrate is indicated by the vertical line between AAG/AAG and the numbers in parentheses indicate the first and last nucleotide in the presented structure. FIG. 6a represents normal abl substrate; nt 1–87 are derived from abl exons 1a and 2. FIG. 6b represents the L6 bcr-abl substrate; nt 1–14 are derived from the Bluescript polylinker sequence, nt 15–72 are derived from bcr exon 2, and nt 73–232 are derived from abl exon 2.

The anchor was inserted in order to favor hybridization of the ribozyme to RNAs containing bcr sequences, thus discouraging the ribozyme from cleaving normal abl mRNAs. The anchor may also function to sequester the ribozyme in the vicinity of the cleavage site, a region which may be buried in secondary structure. Anchors of various lengths were tested. Preferred embodiments of the L6(l) ribozymes includes the following ribozymes:
5'GUCAGAUGCCUGAUGAGUCCGUGAGGAC-GAAACUGGCAAGAACCCAAAAACUUCCUUA UU GAUGGUCAGCGGAAUGCUGUG 3' L6(1)$_{31}$ (SEQ ID NO: 2) and
5'GUCAGAUGCCUGAUGAGUCCGUGAGGAC-GAAACUGGCAAGAACCCAAAAACUUCCUUA UU GAUGGUCAGCG 3' L6(1)$_{21}$ (SEQ ID NO: 15) and
5'GUCAGAUGCCUGAUGAGUCCGUGAGGAC-GAAACUGGCAA GAACCCAAAACUUCCUUAUUG 3' L6(1)$_{11}$ (SEQ. ID NO: 14)

The L6(2) class of ribozymes were designed to cut at the CUU motif located seven nucleotides 3' of the bcr-abl junction. The region that is complementary to bcr exon 2, is preferably about 2 to about 500, more preferably about 5 to about 100, and most preferably about 5 nucleotides. The catalytic core sequence is preferably the hammerhead catalytic core motif. In certain preferred embodiments, each of the two legs is about 4 to about 15, preferably about 7 nucleotides in length.

Preferred embodiments of the L6(2) ribozymes include the following ribozymes:
5'GCCGCUGCUGAUGAGUCCGUGAGGAC-GAAAGGGCUUCUUCC 3'(SEQ ID NO: 3);
5'GCCGCUGCUGAUGAGUCCGUGAGGAC-GAAAGGGCCACUUCC 3'(SEQ ID NO: 4).

The complementary sequences can be varied and are different in each of the ribozymes above. The first ribozyme (SEQ ID NO: 3) maintains perfect complementarity to abl exon 2 across the region located 3' of the catalytic sequence, while the second ribozyme listed above contained 2 mismatches to the abl exon 2 sequence. Hybridization of ribozymes containing mismatches of the abl exon 2 sequence to an RNA molecule would presumably be dependent on both the bcr and abl complementary sequence. The preferred number of mismatches with abl sequences are those that allow greater efficiency of cleavage while retaining specificity.

The majority of hammerhead ribozymes described in the literature comprise a hammerhead sequence, flanked by "legs," which are sequences complementary to the target sequence and which flank the catalytic site. The region of complementarity serves to guide the ribozyme to the desired site of cleavage and is, therefore, generally responsible for the specificity of ribozyme cleavage. However, in designing such ribozymes, it is presumed that the regions on the target sequence immediately flanking the catalytic site are "open" for the initial binding, i.e., the nucleation critical to ribozyme function.

The present invention provides, for example, ribozymes capable of cleaving a sequence that is present at a distance from the "open" region of complementarity, such as in CML, ALL and follicular lymphoma where chromosome breakpoints may occur at various locations. These ribozymes include sufficient complementarity on one side of the cleavage site to allow stable hybridization, and similarly sufficient complementarity on the other side of the cleavage site. These regions of complementarity can be attached to a spacer consisting of nucleotides or other molecules, such as polyethylene glycol, that do not substantially hybridize with the sequences of the substrate located between the complementary nucleotide sequences of the ribozyme. The phrase "does not substantially hybridize" signifies that there may be some complementarity present in the spacer sequence so long as it does not hybridize well enough to impede the efficiency of the cleavage reaction.

This region of unmatched nucleotides can serve as a link between the complementary regions of the legs and anchor located at a distance from one another. Thus, these ribozymes would allow cleavage at a distance from one of the complementary regions. In certain preferred embodiments, a longer region of complementarity distant from the cleavage site serves to anchor the ribozyme. The specificity and rate of cleavage of the ribozyme may be modified by changing the extent of base pairing present in any one region of complementarity to the target.

The term "leg" is defined as a region of complementarity which is capable of binding to a complementary region in the substrate mRNA contiguous with the cleavage site. In a preferred embodiment, the region of complementarity on the leg is contiguous with the catalytic sequence of the ribozyme. It is understood that the phrase "capable of binding" encompasses ribozymes with nucleotides that do not precisely match the target mRNA so long as the leg is capable of detectably binding the target region in the substrate. Thus, complementarity may include mismatches so long as the region remains capable of binding the targeted area. The legs of a ribozyme generally function in nucleation and base pair with the substrate thereby allowing the precise positioning of the catalytic domain adjacent to a site for cleavage. Haseloff, et al., Nature 1988, 334: 585–591.

The term "anchor" encompasses a region of complementarity with the substrate mRNA that may be either contiguous with one of the legs (without a spacer in the ribozyme) or noncontiguous with one of the legs (with a spacer in the ribozyme). The anchor is characterized by being capable of binding to a region of the substrate mRNA which can be noncontiguous with the regions of the substrate mRNA complementary to the legs and by effecting nucleation when secondary structure prevents the legs from doing so and/or helping to improve specificity of the legs when the target sequence is in a region distant from the junction in a chimeric RNA. The length of the noncontiguous area on the substrate can be as short as 1 nucleotide, but is preferably at least about 3 nucleotides.

Figure 1B:
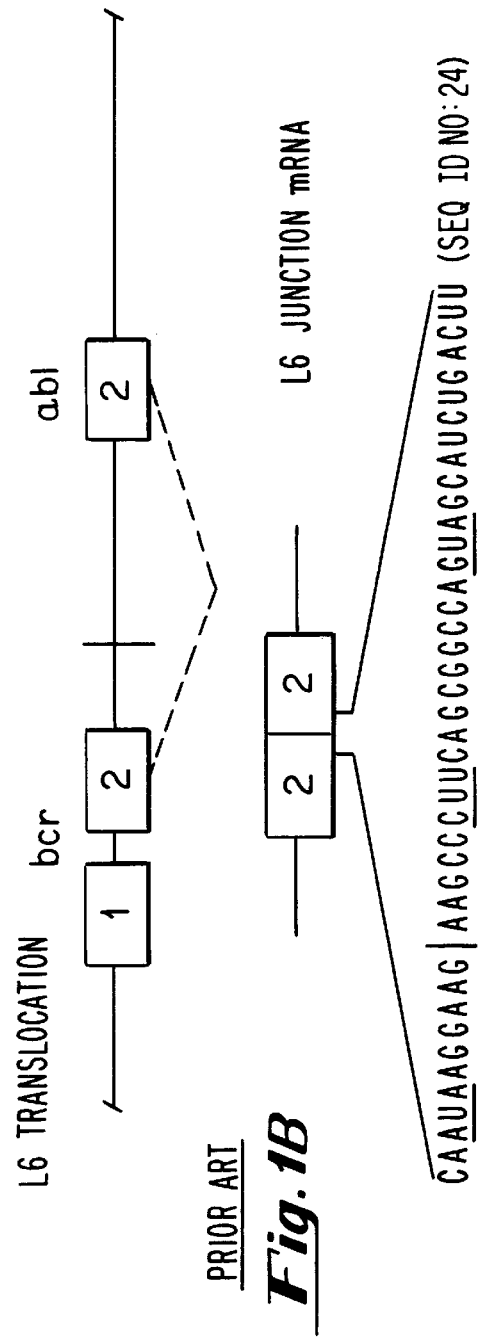

An advantage conferred by ribozymes with an anchor sequence includes, for example, the ability to cleave an aberrant fusion mRNA in which the catalytic recognition sequence in the substrate mRNA is located at a distance from the junction in the substrate fusion mRNA. Fusion RNAs involve a translocation of two chromosomes that places a gene on one chromosome in juxtaposition with a gene on another chromosome. Upon transcription, the translocation thus generates a fusion mRNA. When the catalytic recognition site is near the junction, ribozymes having a leg complementary to each RNA species immediately on either side of the breakpoint can be utilized to target the fusion RNA; presumably, without also cleaving the two native RNA species which it represents. Naturally, as the catalytic recognition site moves farther away from the junction, the possibility that the ribozyme will also cleave the native RNAs increases. As is evident from FIG. 1, all of the cleavage sites on the L6 fusion product are greater than or equal to 7 nucleotides away from the junction.

A ribozyme according to the present invention affords greater specificity for the substrate RNA when the catalytic recognition site is at a distance from the junction. It also provides a mechanism for overcoming obstacles near the catalytic site, such as secondary structure, which inhibit ribozyme cleavage. A general method for preparing such ribozymes is disclosed herein.

The first step in the method of making a ribozyme, when using, for example, the hammerhead catalytic core, is to identify an XUX site (X being any one of the four nucleotides) in the substrate mRNA. The second step is to create the legs of the ribozyme. With a known gene sequence, the ribozyme can be designed so that the legs of the ribozyme are complementary to either side of the XUX site in the substrate mRNA. Preferably, the ribozyme will be designed so that it does not substantially cleave normal mRNA corresponding to the sequences present in the fusion mRNA. The third step involves the creation of an anchor sequence. The anchor sequence can be targeted against a region in a fusion mRNA distant to the catalytic recognition sequence such that the anchor is complementary to a region in a different RNA species than the one with the catalytic target recognition site. A spacer region may optionally be included in the ribozyme. When inhibiting secondary structure is present, the anchor can be designed to be complementary to a region on the substrate RNA immediately 5', 3', and/or even within, this structure.

The anchor allows the ribozyme to recognize and bind to the sequences complementary to the anchor, such as the region of the mRNA corresponding to the translocation, even though the catalytic site is distant from the translocation junction. Even if the size of the ribozyme does not correspond to the size of the substrate mRNA that spans the area between the translocation and the catalytic site, any non-complementary portion of the substrate mRNA may form a localized secondary structure, such as a loop, thus permitting the ribozyme to bind to the noncontiguous sequences.

It will be understood that the ribozyme can be designed to cleave any portion of the substrate mRNA; the targeted region need not be located near the translocation junction. Similarly, the anchor sequence need not be targeted to the translocation junction. Our results indicated that the L6 ribozymes cleaved both the L6 and K28 messages, and that this cleavage was specific for the aberrant messages only. It will also be understood that a single ribozyme can be effective for many different translocations resulting in the same fusion mRNA.

Another example of an advantage conferred by a ribozyme with an anchor sequence is the ability to avoid steric hindrance located near the catalytic recognition sequence in the substrate mRNA, in addition to that due to secondary structure. An example of another situation creating steric hindrance includes the binding of proteins to the substrate mRNA. The presence of secondary structure can be determined, for example, using computer programs such as PC Gene (Intelligenetics, Mountain View, Calif.), and/or by chemical or enzymatic means.

An advantage conferred by ribozymes with a spacer, for example, is its ability to confer flexibity to the ribozyme, thereby allowing it to rotate in space in order to make contact with the substrate mRNA. A spacer also allows ribozymes to span long distances of the substrate mRNA without binding to it.

The spacer region may consist of nucleotides or derivatives thereof or non-nucleotide spacers, such as polyalkylene glycol, as well as the non-nucleotide spacers disclosed in Levenson et al., U.S. Pat. No. 4,914,210, which is hereby incorporated by reference. In certain preferred embodiments, the spacer consists of polyethylene glycol. In other preferred embodiments, the spacer region has 1 to about 3000 nucleotides or derivatives thereof. More preferred embodiments have at least about 13 nucleotides. The phrase "chemical spacer region" means a spacer region having a chemical spacer such as, for example, those chemicals disclosed in U.S. Pat. No. 4,914,210. A specific example is polyalkylene glycol, and more preferably, polyethylene glycol. One skilled in the art can determine whether such a chemical is equivalent in size to 1 to 1,000 nucleotides.

It will be understood that, once armed with the present invention, one skilled in the art will be able to create ribozymes with multiple anchor sequences as well as ribozymes with multiple spacers and combinations of anchors and spacers. In preferred embodiments, the ribozymes have between 1 and about 100 anchor sequences and more preferably between 1 and about 10. Likewise, in preferred embodiments, the ribozymes have between about 1 and 100 spacer regions, and more preferably between 1 and about 10.

In preferred embodiments, each leg of the ribozyme has about 2 to about 15 nucleotides, and preferably about 7 nucleotides. The anchor sequence preferably has about 2 to about 500 nucleotides and more preferably about 5 to about 100 nucleotides. The optional spacer region preferably spans about 1 to 3000 nucleotides of the substrate mRNA, more preferably about 1 to 1000 nucleotides, and most preferably about 10 to about 100 nucleotides.

Once armed with the present disclosure, one skilled in the art would be able to make modifications in the design of these ribozymes in order to increase the efficiency and/or specificity of the cleavage reaction. These modifications include, for example, in the case of CML, increasing the size of the region which is complementary to bcr exon 2 and/or decreasing the amount of complementarity to abl exon 2.

In certain preferred embodiments, the ribozymes include multiple catalytic units. Given the present disclosure, one skilled in the art is capable of making ribozymes having multiple catalytic units which are capable of cleaving the substrate mRNA, such as the K28 mRNA and/or L6 mRNA. Such ribozymes may include spacer regions between the catalytic units in addition to regions of complementarity with the substrate mRNA. The catalytic units themselves may cleave, for example, abl and/or bcr sequences.

Examples of ribozymes with a spacer region joining the anchor to one of the legs include ribozyme $L6(1)_{31}$ (SEQ ID NO: 2) in Example 1 and ribozymes $L6(2)_0$ and $L6(2)_2$ in Example 2 (SEQ ID NO: 4 and 5). Preferred embodiments include the ribozymes of SEQ ID NO: 14 and SEQ ID NO: 15 which are modifications of SEQ ID NO: 2 having shorter anchor sequences and which cleave the substrate mRNA more efficiently.

Another example of a ribozyme capable of cleaving a fusion mRNA generated from a translocation is the ribozyme of SEQ ID NO: 13. This ribozyme is targeted against a fusion mRNA involved in ALL and may be used in the treatment of ALL. A 9;22 chromosomal translocation is associated with ALL. The breakpoints on chromosome 9 lie upstream of abl exon 2. Transcription through this region yields a fusion mRNA in which the first bcr exon is adjacent to abl exon 2. The anchor of this ribozyme is complementary to bcr exon 1, and the remainder of the ribozyme corresponds to the spacer region, legs and catalytic sequence of SEQ ID NO: 2.

Given the present disclosure, one skilled in the art would also be able to create a ribozyme targeted against, for example, follicular lymphoma and other diseases involving translocations.

It will also be understood that the ribozymes may be modified, for example, by using 2'-O-alkyl- and 2'-O-allyl-ribonucleotide analogues. Paolella et al., EMBO J. 1992, 11, 1913–1919. Such modifications are included within the term "derivatives." Additionally, mixed deoxyribonucleotides and ribonucleotides may be used. Perreault et al., Nature 1990, 344, 565–567.

Further, known catalytic sequences may be altered. For example, the consensus sequence in the core catalytic region of the hammerhead ribozyme may be changed, e.g., according to Ruffner et al., Biochemistry 1990, 29, 10695–10702.

The present invention also provides methods for treating vertebrates suspected of having CML or ALL wherein it is believed that the vertebrate's hematopoietic cells express L6 mRNA. Preferred embodiments involve using oligonucleotide therapeutics capable of decreasing the expression of L6 mRNA or both the L6 and K28 mRNAs. The term "oligonucleotide therapeutics" includes both ribozymes and antisense RNA. In certain preferred embodiments, the oligonucleotide therapeutic comprises a ribozyme capable of cleaving L6 mRNA. In another preferred embodiment, the oligonucleotide therapeutic comprises an antisense oligonucleotide capable of binding the K28 and an antisense oligonucleotide capable of binding the L6 mRNA. A further preferred embodiment provides a mixture of ribozymes and antisense oligonucleotides specific for the K28 and L6 mRNAs. In another preferred embodiment, the "oligonucleotide therapeutic" comprises a ribozyme capable of cleaving both L6 and K28.

Antisense technology provides a valuable tool that can be used to interfere with the expression of specific genes. Antisense oligonucleotides having sequences that are complementary to sequences of the mRNA of a gene of interest can lead to modifications of the phenotype of the cell.

Antisense oligonucleotides which hybridize to at least a portion of the K28 and L6 junctions are contemplated in the methods of the present invention. Thus, molecules which bind competitively to an aberrant transcript are envisioned for therapeutics.

While any length antisense oligonucleotide may be utilized, sequences shorter than 15 bases may be less specific in hybridizing to the target and may be more easily destroyed by enzymatic degradation. Hence, oligonucleotides having at least 15 nucleotides are preferred. On the other hand, the size of the oligonucleotide is limited by its ability to enter the target cell since it is known in the art that large oligonucleotides may be somewhat less effective in interfering with expression because of decreased uptake by the target cell. It will be understood that interference with expression means that there is a detectable decrease in expression of the protein product encoded by the bcr-abl fusion transcript either ex vivo or in vivo.

The term "oligonucleotide" as used herein includes both ribonucleotides and deoxyribonucleotides, and includes molecules which may be long enough to be termed "polynucleotides." Oligodeoxyribonucleotides are preferred since oligoribonucleotides are more susceptible to enzymatic attack by ribonucleases than deoxyribonucleotides. It will also be understood that the bases, sugars or internucleotide linkages may be chemically modified by methods known in the art. Modifications may be made, for example, to improve stability and/or lipid solubility. For instance, it is known that enhanced lipid solubility and/or resistance to nuclease digestion results by substituting a methyl group or sulfur atom for a phosphate oxygen in the internucleotide phosphodiester linkage. The phosphorothioates, in particular, are stable to nuclease cleavage and soluble in lipid.

The ribozymes and the antisense oligonucleotides of the present invention may be synthesized by any of the known chemical oligonucleotide synthesis methods. See for example, Gait, M. J., ed. (1984), Oligonucleotide Synthesis (IRL, Oxford). Both the ribozymes and the antisense oligonucleotides may also be synthesized through recombinant expression from an appropriate vector.

Preferred embodiments of the present invention involve targeting the L6 mRNA alone or both the L6 mRNA and the K28 mRNA in a combination treatment. In preferred methods for treating CML or ALL, oligonucleotide therapeutics are used to decrease expression of the targeted mRNAs. The phrase "capable of decreasing expression" signifies a detectable decrease in expression.

Combination therapy is especially important to those patients having the K28 translocation who express both the L6 and K28 mRNAs either simultaneously or consecutively during the course of the disease. Treatment with a therapeutic agent specific for either the L6 or the K28 mRNA would most likely be ineffective in these patients.

A preferred method comprises a combination therapy having components specific for both the K28 and L6 mRNAs. Methods of treatment include, for example, a mixture of ribozymes capable of cleaving the K28 and L6 mRNAs.

Another preferred embodiment is a method of treatment of ALL or CML using antisense oligonucleotides containing components capable of binding both the K28 and L6 mRNAs. The phrase "capable of binding" indicates detectable binding in assays known to one skilled in the art, such as a shift in mobility during electrophoresis.

A further preferred embodiment provides a mixture of ribozymes and antisense oligonucleotides specific for the K28 and L6 mRNAs. These treatments may also be used, for example, in conjunction with conventional therapies such as chemotherapy and irradiation.

A further preferred embodiment provides a single ribozyme capable of cleaving L6 and K28.

A further preferred embodiment involves a combination treatment directed against c-myc expression in addition to targeting the K28 and/or L6 mRNAs. The potential role of c-myc in CML is discussed, for example, in Sawyers et al., Cell 1992, 70, 901–910. Specifically, myc affects the transformation ability of bcr-abl in vitro and myc has been implicated in some patients with blast crisis of CML. Therefore, certain embodiments of the present invention comprise a combination treatment for those patients also expressing c-myc using a treatment such as antisense oligonucleotides or ribozymes specific for c-myc RNA along with antisense oligonucleotides and/or ribozymes specific for the K28 and/or L6 mRNAs.

In other preferred embodiments, the ribozyme of SEQ ID NO: 13 may similarly be used in the treatment of ALL. The substrate mRNA for this ribozyme is provided in SEQ ID NO: 12.

For in vivo use, the antisense oligonucleotides as well as the ribozymes may be combined with a pharmaceutical carrier, such as a suitable liquid vehicle or excipient and an optional auxiliary additive or additives. The liquid vehicles and excipients are conventional and commercially available. Illustrative thereof are distilled water, physiological saline, aqueous solution of dextrose, and the like.

In addition to administration with conventional carriers, the antisense oligonucleotides as well as the ribozymes may be administered by a variety of specialized oligonucleotide delivery techniques. For example, oligonucleotides have been successfully encapsulated in unilamellar liposomes. Reconstituted Sendai virus envelopes have been successfully used to deliver RNA and DNA to cells. Arad et al., *Biochem. Biophy. Acta.* 1986, 859, 88–94 (incorporated herein by reference). Additionally, oligonucleotides may be carried into the cell by exploitation of folate receptor-mediated endocytosis. Leamon and Low, *Proc. Nat'l. Acad. Sci.* 1991, 88, 5572–5576 (incorporated herein by reference).

It will also be understood that the ribozyme and antisense oligonucleotides may be administered by vector-mediated delivery. Such delivery systems are within the scope of one skilled in the art once armed with the present disclosure. Preferred methods of gene therapy include, for example, the incorporation of the gene encoding the therapeutic oligonucleotide into a retroviral vector, followed by selection of cells expressing the gene. Using the retroviral vector, the gene is then transferred into the stem cells of the patient'ss bone marrow ex vivo. In order to effect repopulation, the patient'ss own bone marrow is treated, for example, with irradiation, chemotherapy or ablation. The treated bone marrow is then transplanted into the patient.

For examples of vector-mediated delivery systems, see, Rosenberg, et al., *New Eng. Jour. Med.* 1990, 570–578; Roux, et al., *Proc. Natl. Acad. Sci.* 1989, 86, 9079–9083; DeMonte, et al., *Proc. Natl. Acad. Sci.* 1990, 87, 2941–2945; Hantzopoulos, et al., *Proc. Natl. Acad. Sci.* 1989, 86, 3519–3523 and Kashani-Sabet, et al., *Antisense Res. and Dev.* 1992, 2, 3–15.

For in vivo use, the antisense oligonucleotides as well as the ribozymes may be administered in an amount effective to reduce expression of aberrant transcripts. The actual dosage administered may take into account the size and weight of the patient, whether the nature of the treatment is prophylactic or therapeutic in nature, the age, weight, health and sex of the patient, the route of administration, and other factors.

It is also possible to administer the antisense oligonucleotides as well as the ribozymes ex vivo by isolating white blood cells from peripheral blood, treating them with the oligonucleotides, then returning the cells to the donor'ss blood. Ex vivo techniques have been used in the treatment of cancer patients with interleukin-2 activated lymphocytes.

The oligonucleotide therapeutics may be administered in amounts effective to kill leukemic cells while maintaining the viability of normal hematologic cells. Such amounts may vary depending on the nature and extent of the leukemia, the particular oligonucleotide utilized, the relative sensitivity of the leukemia to the oligonucleotide, and other factors.

It will be understood that the treatments of the present invention may be combined with conventional therapies. It will also be understood that the combination treatments of the present invention may be administered sequentially or simultaneously. Dosage determinations will depend upon the individual and can be determined by one skilled in the art.

MATERIALS AND METHODS

Growth and Maintenance of Bacteria *Escherichia coli* strains HB 101 (Boyer, H. W. and D. Roulland-Dussoix, *J. Mol. Bio.* 1969, 41, 459) and SB 221 (Nakamura, D. and M. Inouye, *Cell* 1979, 18, 1109–1117) were grown in L broth (10 g/l tryptone, 5 g/l yeast extract, 10 g/l NaCl) at 37° C. For long term storage, bacterial stocks were stored in 75% L broth/25% glycerol at −80° C.

Plasmid

Bluescript II KS+was purchased from Stratagene and maintained in HB 101 which was grown in L broth containing 100 µg/ml ampicillin.

Construction of Template DNA

Two DNA templates for each ribozyme were synthesized as two complementary oligodeoxynucleotides with EcoR1 ends on a Milligen BioSearch 8750 DNA synthesizer, as a sianoethylphosphoroamidite synthesis (Beaucage, S. and M. Caruthers, *Tetrahedron Lett.* 1981, 22, 1859–1862) and were purified by reverse phase High Pressure Liquid Chromotography (HPLC). Approximately three micrograms of each oligonucleotide was phosphorylated in 1×linker-kinase buffer (70 mM Tris-Cl, pH 7.6, 1 mM ATP, 10 mM $MgCl_2$, 15 mM DTT) containing 50 units of T4 polynucleotide kinase (United States Biochemicals). The reactions were carried out at 37° C. for 30 minutes.

Complementary oligonucleotides were annealed to each other following phosphorylation by combining reaction mixes and incubating sequentially at the following temperatures for the indicated times: 85° C. for 5 minutes; 65° C. for 15 minutes; 37° C. for 15 minutes; room temperature for 15 minutes; and on ice for 15 minutes. The annealed phosphorylated oligonucleotides were ethanol precipitated and resuspended in deionized water ($dH_2O$) at a concentration of 75 ng/µl. Once annealed, the double stranded oligonucleotides were ligated into the EcoR1 site of Bluescript II KS +. Ligated DNA was electroporated into BH 101 bacteria using the "gene pulse" (Bio Rad) according to the manufacturer'ss instruction. Single stranded overhanging ends complementary to ends generated by EcoR1 digestion of DNA.

Construction and Cloning of Substrate DNAs

The DNA template for the L6 bcr-abl substrate RNA was synthesized as an oligodeoxynucleotide having the same polarity as L6 bcr-abl mRNA. This DNA oligonucleotide is comprised of a sequence that maps from a position located 57 nts 5' of the bcr-abl junction to a position located 97 nts 3' of the bcr-abl junction (Shtivelman, et al., *Cell* 1986, 47, 277–284; Heister Kamp, et al., *Nature* 1985, 315, 758–761.). Double stranded DNA was synthesized by the polymerase chain reaction (PCR) using 5' and 3' primers which have the following sequences:

5' ATTGCGATAGGATTGAATTCAACTCGT-GTGTGAAACTCCA 3' (SEQ ID NO: 16) and

5' AATGCGATAGGATTGAATTCGTCCAGC-GAGAAGGTTTTCC 3' (SEQ ID NO: 17)

,respectively. (EcoR1 sites are underlined). PCR products were gel purified, EcoR1 digested, and then cloned into Bluescript II KS+ as already described.

The DNA template for normal bcr substrate RNA was synthesized as an oligodeoxynucleotide having the same polarity as bcr mRNA. Double stranded DNA was synthesized by PCR using 5' and 3' primers which have the following sequences:

5'ATTGCGATAGGATTGAATTCAAGCT-TAAGTGTTTCAGAAGCTTCTCCCTGACATCCGT GGAGCTGCA 3' (SEQ ID NO. 18)

5'AATGCGATAGGATTGAATTCCGGAGACT-CATCATCTTCCTTATTGATGGTCAGCGGAA TGC 3' (SEQ ID NO: 19), respectively. The resulting PCR product maps from position 554 to position 675 of normal bcr cDNA (Lozzio, et al., *Blood*, 1975, 45, 321–334).

A region of normal abl mRNA from K562 cells (Lozzio, et al.) was amplified by reverse transcriptase PCR (Innis, et al., *PCR Protocols*, A Guide to Methods and Applications, 1990). The sequence of the abl cDNA primer 5 is: 5'TAG-GACTGCTCTCACTTCTCACG 3' (SEQ ID NO: 20). Abl specific cDNA was amplified by PCR. The sequences of the 5' and the 3' primers are 5' ATCTGCCTGAAGCTG-GTGGGCTGC 3' ( SEQ ID NO: 21) and 5' ATGCTTA-GAGTGTTATCTCCACT 3' (SEQ ID NO: 22) respectively. The resulting PCR product maps from position 157 to position 340 of normal abl cDNA (5).

The normal bcr and abl PCR products were gel purified, phosphorylated and then blunt ended in the presence of dNTPs and the Klenow fragment of DNA polymerase.

The DNA was then cloned into the Hinc II site of Bluescript II KS+.

The template for the K28 substrate was provided by Dr. Scott Shore (Temple University, Philadelphia, Pa.).

Preparation of Cloning Vector

Bluescript II KS+ plasmid DNA was digested to completion with either Hinc II or EcoRI (New England Biolabs) using conditions recommended by the manufacturer. The digested DNA was extracted twice with phenol:chloroform, ethanol precipitated, and then dephosphorylated with Calf Intestinal Phosphatase (Boehringer Mannheim Biochemicals) according to the conditions recommended by the supplier.

Ribozyme Cloning

Between 150 ng and 450 ng of annealed oligonucleotide was ligated with EcoRI-digested Bluescript II KS+ in 10 µl of 1×ligation buffer (50 mM Tris Cl, pH 7.6, 10 mM $MgCl_2$, 1 mM ATP, 10 mM DTT) containing 200 ng of vector DNA and 5 µl of T4 DNA ligase (Boehringer Mannheim Biochemicals). Following an overnight incubation at 14° C, the reaction was diluted with 5 µl of TE (10 mM Tris-Cl, pH 7.7, 1 mm EDTA) and used immediately or stored at −20° C.

Two microliters of the diluted ligation reactions were electroporated into HB 101 or SB 221 in a Bio-Rad "Gene Pulser" according to the manufacturers instructions. Transformed bacteria were immediately diluted in 1 ml of SOC medium (2% [w/v] Bacto Tryptone, 0.5% [w/v] yeast extract, 10 mM NaCl, 10 $MgSO_4$-7$H_2O$, 20 mM glucose) and incubated at 37° C. for one hour. Transformed bacteria were then plated on an L agar plate containing 100 µg/ml ampicillin and incubated at 37° C. overnight.

Characterization of Clones

Individual transformants were picked and grown in LB medium containing 100 µg/ml ampicillin. Plasmid DNA was harvested from bacterial cultures according to the alkaline lysis protocol (Sambrook, J. Fritsch, E. F. and Maniatis, T. (eds.), *Molecular Cloning, A Laboratory Manual*, Cold Spring Harbor, N.Y., Cold Spring Harbor Laboratory, 1989). DNA was further purified by lithium chloride precipitation, digestion with RNase A, polyethylene glycol precipitation, extraction with phenol and chloroform and then precipitation with ethanol (Sambrook, J. Fritsch, E. F. and Maniatis, T. (eds.), *Molecular Cloning, A Laboratory Manual*, Cold Spring Harbor, N.Y., Cold Spring Harbor Laboratory, 1989). DNA was resuspended in d$H_2O$ at a concentration of 1 µg/l to 2 µg/l.

Aliquots of plasmid DNA were double digested with Pstl (New England Biolabs) and HindIII (New England Biolabs) according to the manufacturer'ss directions. Products were electrophoresed through 1.5% agarose/TBE (90 mM Trisborate, 2 mM EDTA) gels at 70 mamps.

Sequence Analysis

Plasmid inserts of the appropriate size were subjected to DNA sequence analysis using Sequenase (United States Biochemical) and both the $M13^{-20}$ and reverse primers according to established protocol (Sambrook, J. Fritsch, E. F. and Maniatis, T. (eds.), *Molecular Cloning, A Laboratory Manual*, Cold Spring Harbor, N.Y., Cold Spring Harbor Laboratory, 1989). Products of the sequencing reaction were electrophoresed through a 7% polyacrylamide/urea gel (Sambrook, J. Fritsch, E. F. and Maniatis, T. (eds.), *Molecular Cloning, A Laboratory Manual*, Cold Spring Harbor, N.Y., Cold Spring Harbor Laboratory, 1989).

Template Preparation for T7 and T3 Transcription

Plasmid DNAs were digested to completion with either HindIII, Pst1, BamHI, or XhoI (New England Biolabs) according to the manufacturer'ss directions. Digested DNA was ethanol precipitated and resuspended in 200 µl of 1×Proteinase K buffer (10 mM Tris-Cl, pH 8.0, 5 mM EDTA, 0.5% SDS) containing 1 µl of a freshly made Proteinase K solution (10 mg/ml) (Sigma).

The reactions were incubated at 37° C. for 30 minutes and then extracted twice with phenol:chloroform. DNA was ethanol precipitated and resuspended in RNase free $H_2O$ (Sambrook, J. Fritsch, E. F. and Maniatis, T. (eds.), Molecular Cloning, *A Laboratory Manual*, Cold Spring Harbor, N.Y., Cold Spring Harbor Laboratory, 1989) at a concentration of 500 ng/µl.

In Vitro Transcription

The substrate and ribozyme RNAs were transcribed from the Bluescript II Ks + template using either T3 RNA polymerase (Promega) or T7 RNA polymerase (Promega) according to instructions provided by the manufacturer. Following transcription, the DNA templates were removed from the reaction by adding RNase free DNase (Worthington Biochemical) at 5 µg/µl or 2 units per µg of DNA template and incubating at 37° C. for 30 minutes. RNA was concentrated by ethanol precipitation and then subjected to proteinase K digestion, and resuspended in RNAse Free $H_2O$. Substrate RNAs used as tracers in ribozyme cleavage experiments were radiolabelled during T7 or T3 transcription with [$a^{32}P$] CTP (Amersham) according to the manufacturers recommended procedure.

Ribozyme Assays

Ten picomoles of both ribozyme and substrate RNAs were incubated in 10 µl of 1×ribozyme reaction buffer (50 mM Tris-Cl, pH 7.5, 10 mM $MgCl_2$) containing either 10 mM vanadylribonucleoside complexes or 40 units of RNasin (Promega). Reactions were incubated at 37° C. for 13–15 hours and terminated by the addition of 10 µl formamide loading buffer (80% formamide, 10 mm EDTA, 1 mg/ml xylene cyanol FF, 1 mg/ml bromophenol blue). Samples were denatured at 95° C. for two minutes prior to denaturing polyacrylamide gel electrophoresis. Alternatively, ten pmole of both ribozyme and substrate RNAs were incubated in 10 µl of ribozyme reaction buffer (50 mM Tris-Cl, pH 7.5, 10 mM $MgCl_2$) containing 50,000 cpm of radiolabelled substrate RNA (specific activity [$5 \times 10^8$ cpm/µg]) as tracer. Reactions were incubated at 37° C. for up to 10 hours and terminated by freezing on dry ice. Samples were subjected to denaturing polyacrylamide gel electrophoresis on 5% polyacrylamide gels (Boyer,P. D., 1970, *The Enzymes*, Student Ed., Academic Press, Inc., New York, N.Y.) ). Gels were dried and subsequently analyzed with a PhosphorIager (Molecular Dynamics) according to the manufacturer'ss directions.

Gel Shift Analysis

Fifty pmole of ribozyme and 10 pmole of substrate were incubated in 10 μl of ribozyme reaction buffer containing 50,000 cpm of radiolabelled substrate RNA (specific activity [$5\times10^8$ cpm/μg]) at 37° C. for 2.5 hours. Products were analyzed by native gel electrophoresis (non-denaturing) on a 6% polyacrylamide gel in 1×TBM buffer (90 mM Tris-borate, 10 mM $MgCl_2$). Gels were dried and subsequently analyzed with a PhosphorImager (Molecular Dynamics). All ribozymes shifted the substrate bcr-abl bands. Two conformational species of bcr-abl were detected.

Kinetic Analysis

Ribozyme reactions were carried out as described above but in the presence of substrate excess. The ribozyme concentration was held constant at 0.5 μM. The various substrate to ribozyme ratios used are described below. Reactions were terminated at various times and the products subjected to denaturing gel electrophoresis. Gels were dried and subsequently analyzed with a PhosphorImager.

RNA Folding

Secondary structures were predicted for ribozymes and substrate RNAs using the programs of Zucker and Steigler, on PC Gene (Intelligenetics) and MacDNASIS Pro (Hitachi).

Cells

K562 cells (Blood, 1975, 45, 321–334) were obtained from the American Type Culture Collection (ATCC #CCL 243) and were cultured in complete minimal essential medium (JRH Biosciences) supplemented with 10% Fetal Bovine Serum (Gibco-BRL).

EXAMPLE 1

The L6(1) Ribozymes and their substrate are listed below; the recognition sequence in the substrate cleaved by this ribozyme is indicated in bold, the spacer sequence in the ribozyme is underlined, the junction is symbolized by | [0a‰1]nd the catalytic core is indicated by brackets.

nucleotide spacer sequence. This spacer bears no complementarity to either abl or bcr sequences. The hammerhead catalytic core, located near the 5' end of the ribozyme, lies within a 15 nt sequence that is complementary to abl exon 2. A control ribozyme which lacks an anchor sequence, but is otherwise homologous to the anchored ribozymes, was also constructed and tested (SEQ ID NO: 23).

Figures 4A, 4B, 4C:
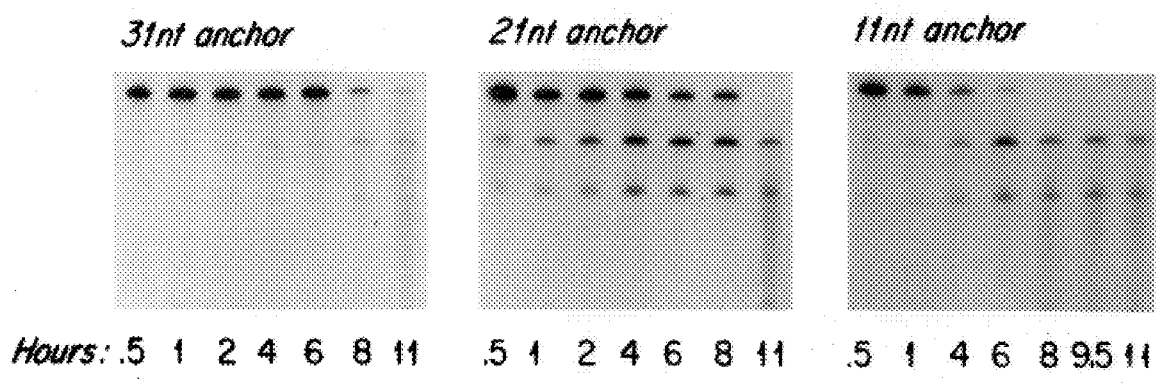
FIGS. 4 a–c depict the time course of the cleavage of the bcr-abl substrate by ribozymes L6(1)$_{31}$, L6(1)$_{21}$, and L6(1)$_{11}$, respectively.

These ribozymes have been designed to cleave the L6 bcr-abl mRNA at the GUA triplet located 19 nts 3' of the bcr-abl junction. Cleavage at this site in the synthetic substrate generates two fragments which are 143 nt and 85 nts in length (consisting of 77 or 73 nucleotides of substrate and 66 or 12 nucleotides of polylinker, respectively). Each of the ribozymes was able to cleave the L6 substrate into the expected cleavage products, and the amount of substrate cleaved by each ribozyme, was, in general, inversely related to the length of the anchor sequence. FIGS. 4 a-c depict the time course of the cleavage products for the $L6(1)^{31}$, $L6(1)^{21}$, and $L6(1)^{11}$ ribozymes, respectively. Substrate bands are indicated with an "S". Product bands are indicated with a "P". The 21 nt anchor ribozyme, however, demonstrated more activity than the 11 nt anchor ribozyme at the earlier time points. The ribozyme not having an anchor also correctly cleaved the L6 substrate. Cleavage was less efficient than with an anchor and less product formation was observed. No cleavage products were detected in the absence of ribozyme.

None of the anchor sequences prevented the correct cleavage of the L6 substrate. Kinetic analysis, however, indicated that product release, the rate limiting step in the cleavage reactions, was slower in reactions catalyzed by ribozymes with longer anchors. The initial burst rate was similar for both the 11 nt anchored and the 21 nt anchored ribozyme when reactions were carried out under conditions of substrate excess. These rates are slower than the rates measured for other ribozymes (*Proc. Natl. Acad. Sci. USA* 1990, 87, 1668–1672; *Biochemistry,* 1992, 31, 12042–12054.) However, the rates of the anchored

```
(5'CACAGCAUUCCGCUGACCAUCAAUAAGGAAG|AAGCCCUUCAGCGGCCAGUAGCAUCU     (SEQ ID NO: 1)

GACUU 3'

3' GUGUCGUAAGGCGACUGGUAGUUAUUCCUUC|AAAAACCCAAGAACGGUCA            (SEQ ID NO: 2)

[AAGCAGGAGUGCCUGAGUAGUC]CGUAGACUG 5' L6(1)₃₁

3' GUUAUUCCUUC|AAAAACCCAAGAACGGUCA                                (SEQ ID NO: 14)

[AAGCAGGAGUGCCUGAGUAGUC]CGUAGACUG 5' L6(1)₁₁

3' GCGACUGGUAGUUAUUCCUUC|AAAAACCCAAGAACGGUCA                      (SEQ ID NO: 15)

[AAGCAGGAGUGCCUGAGUAGUC]CGUAGACUG 5' L6(1)₂₁
```

Cleavage of the L6 substrate in vitro using $L6(1)_{31}$ resulted in the production of the expected cleavage products described above. Fifteen to forty percent of the substrate was cleaved using equimolar amounts of ribozyme and substrate. The remainder of the substrate migrated as an uncleaved species of approximately 230 bp. Increasing the ratio of ribozyme:template approximately 3-fold resulted in a slight increase in the amount of cleavage product generated. This ribozyme is apparently specific for the L6 substrate since no cleavage of the K28 substrate was detected.

The L6(1) class of hammerhead ribozymes, depicted in FIG. 2, sequences listed above, comprised anchors located at the 3' end of the ribozyme complementary to the region of bcr exon 2 of 31, 21, or 11 nucleotides in length. They were connected to the 5' portion of the ribozyme by means of a 13 ribozymes were measured in reactions using a large substrate RNA molecule while the rates reported for the other ribozymes were determined in reactions using a small oligoribonucleotide substrate. The 21 nt anchored ribozyme was more active than the 11 nt anchored ribozyme when reactions were carried out under conditions of ribozyme excess. Under these conditions, the rate of cleavage by each ribozyme was slower than the rate measured in reactions where substrate was in excess indicating that the ribozymes may undergo a substrate induced conformational change (ie. see *Nucleic Acids Res.* 1990, 18, 1103–1108. However, for therapeutic purposes, it is advantageous that the ribozymes are more efficient at substrate excess. The 21 nt anchored ribozyme has a slower product dissociation rate than does the 11 nt anchored ribozyme, however, and the net result is that the 11 nt anchored ribozyme is more efficient over an extended reaction time.

The ribozymes are specific for bcr-abl mRNA. Secondary structure predictions for substrate RNAs were generated using the Zucker and Steiger algorithm for RNA folding. Secondary structure predictions for normal abl RNA suggest that the sequences flanking the cleavage site may not be accessible for ribozyme binding (FIG. 6a). This was confirmed experimentally utilizing an in vitro binding assay. We predicted that the ribozymes would cleave the normal abl substrate if the secondary structure of the substrate was first melted. Experiments were therefore carried out in which the substrate was first denatured and then renatured in the presence of ribozyme. Under these conditions, between 15 and 20% of the normal abl substrate was cleaved by the 11 nt anchored ribozyme. This result, together with the gel shift data, support the interpretation that the normal abl substrate is folded in a way that occludes ribozyme nucleation. It is therefore likely that the anchored ribozymes failed to cleave normal abl RNA because it is inaccessible for ribozyme binding.

Secondary structure predictions for the L6 bcr-abl substrate suggest that the sequences flanking the ribozyme cleavage site are also inaccessible for ribozyme binding but that most of the region complementary to the ribozyme anchor is available for anchor hybridization (FIG. 6b). Although these predictions were generated for a substrate RNA that contains a vector derived polylinker sequence, predictions made for the native substrate RNA indicated that most of the anchor complement is available in this molecule as well. According to our model, the function of the ribozyme anchor is to tether the ribozyme to an accessible substrate sequence thereby sequestering the molecule in the vicinity of the substrate cleavage site. This would allow the ribozyme to cleave the substrate whenever the cleavage site and flanking sequences become available due to temporary transitions in secondary structure. These alternate secondary structures may actually be fostered and/or stabilized by further ribozyme interactions.

Although we have used a chimeric RNA to demonstrate the utility of a ribozyme anchor in overcoming an obstruction caused by the secondary structure around a cleavage site, an anchor could potentially be used to target ribozymes to occluded sites in any RNA molecule.

The optimal length of an anchor is probably dependant upon the anchor sequence and the secondary structure. The presence of some form of anchor is clearly important as inefficient cleavage was observed with the anchor-minus ribozyme. The anchors we tested in this example were attached to the ribozyme via a 13 nucleotide spacer. Anchors might also be connected via a chemical spacer or simply linked directly to the ribozyme. The presence of a spacer may be sterically important in cases in which a ribozyme is tethered at a position distant from the cleavage site.

Tests revealed that, unexpectedly, $L6(1)_{11}$ also cleaved the K28 substrate. This was demonstrated by incubating $L6(1)_{11}$ with the K28 substrate. The reaction products were electrophoresed through a denaturing 5% polyacrylamide gel and visualized with ethidium bromide. Thus, while not cleaving native abl or bcr, $L6(1)_{11}$, cleaved both L6 and K28. Considering the potential variation in the K28 transcript during the course of disease, $L6(1)_{11}$ could be a valuable therapeutic.

EXAMPLE 2

The L6(2) ribozymes ($L6(2)_{0-4}$) are depicted in FIG. 3. Their sequences and substrate are listed below; the recognition sequence in the substrate cleaved by these ribozymes is indicated in bold, mismatched sequences in the ribozymes are underlined, the junction is symbolized by | and the catalytic core is indicated by brackets.

```
5'CACAGCAUUCCGCUGACCAUCAAUAAGGAAG|AAGCCCUUCAGCGGCCAGUAGAUCU     (SEQ ID NO: 1)

GACUU 3'

3'CCUUC|UUCGGGA[AAGCAGGAGUGCCUGAGUAGUC]GUCGCCG 5'              (SEQ ID NO: 3)

L6(2)0

3'CCUUC|ACCGGGA[AAGCAGGAGUGCCUGAGUAGUC]GUCGCCG 5'              (SEQ ID NO: 4)

L6(2)2

3'CCUUC|ACAGGGA[AAGCAGGAGUGCCUGAGUAGUC]GUCGCCG 5'              (SEQ ID NO: 5)

L6(2)3

3'CCUUC|ACAAGGA[AAGCAGGAGUGCCUGAGUAGUC]GUCGCCG 5'              (SEQ ID NO: 6)

L6(2)4.
```

Cleavage of the substrate in vitro using $L6(2)_0$ resulted in complete cleavage of both the L6 and the K28 substrate at the expected cleavage site.

$L6(2)_2$ cleaved the L6 substrate, albeit inefficiently. Inefficient cleavage of the K28 substrate was also observed. An increase of the molar ratio of ribosome with respect to substrate increased the efficiency of the cleavage reaction; however, it remained nonspecific.

$L6(2)_3$ and $L6(2)_4$ did not detectably cleave either the K28 or L6 substrate.

The L6(2) class of hammerhead ribozymes is comprised of a sequence complementary to bcr exon 2, the hammerhead catalytic core and two regions that are complementary to abl exon 2. The region on bcr exon 2, to which the anchor is complementary, is contiguous with the region of substrate RNA complementary to one of the legs. The first abl complementary region is located at the extreme 5' end of the ribozyme while the second region of abl complementarity is situated immediately 3' to the catalytic sequence. The sequence of this region varies in each of the ribozymes of the series. The $L6(2)_0$ ribozyme maintains perfect complementarity to abl exon 2, and ribozymes, $L6(2)_2$, $L6(2)_3$ and $L6(2)_4$, contain 2, 3, or 4 mismatches, respectively, to the abl exon 2 sequence.

These ribozymes have been designed to cleave at the CUU triplet located 7 nt 3' of the bcr-abl junction. Cleavage at this site in the synthetic substrate results in the generation of two fragments which are 131 nts and 97 nts in length (consisting of 65 or 85 nucleotides of substrate and 66 or 12 nucleotides of polylinker, respectively). Although both the L6(2)$_0$ and L6(2)$_2$ ribozymes cleaved the synthetic L6 substrate into the expected cleavage products, the L6(2)$_0$ ribozyme was more active. Unexpectedly, both ribozymes were also able to correctly cleave a synthetic K28 substrate as efficiently as they cleaved the L6 substrate. The L6(2)$_3$ and L6(2)$_4$ ribozymes had no detectable activity.

The L6(2)$_0$ ribozyme is more active than the L6(1)$_{31}$ ribozyme, but less active than both the 21 nt and 11 nt anchored ribozymes of Example 1 at time points analyzed between 0.5 and 4 hours. By 8 hours however, L6(2)$_0$ had cleaved more substrate than the 21 nt anchored ribozyme.

These ribozymes were specific for bcr-abl mRNA but were not as active as the L6(1) ribozymes in cleavage analyzed at early time points. The L6(1) ribozymes contained a spacer and longer anchor sequences. The lower activity of the L6(2) ribozymes was, in part, due to reduced substrate binding as is demonstrated by the gel shift assay. These ribozymes appeared to bind significantly to only one of the conformational species of the L6 bcr-abl substrate. However, most of the substrate was cleaved by the L6(2)$_0$ ribozyme after 8 hours suggesting that the secondary structure of the substrate may not be static and may shift into another conformation that allows ribozyme binding. This demonstrated one advantage of anchored ribozymes--maintaining the cleavage core in proximity so that when conformational shifts make target cites otherwise unavailable available.

The secondary structure predictions indicate that the cleavage site and flanking abl sequence recognized by the L6 (2) ribozymes may not be accessible to these ribozymes (FIG. 6b). However, a region of bcr complementary to the 3' end of the ribozymes as well as one nucleotide of abl does appear to be accessible in the predicted RNA conformation. This region may not be available in the second conformational species of the L6 substrate RNA that is not bound by the ribozymes.

Although L6(2)$_3$ and L6(2)$_4$ did not appear active in the present testing, they may respond differently if synthesized chemically without polylinker sequences. The L6(2)$_0$ and L6(2)$_2$ ribozymes were also able to cleave a synthetic K28 substrate as efficiently as they cleaved the L6 substrate. The ribozymes according to the invention are the first reported to specifically cleave both the L6 and the K28 fusion mRNAs and thus could potentially be used as a single therapeutic to treat cases of CML associated with either a K28 or L6 type translocation.

EXAMPLE 3

Specificity and Efficiency

Figures 5A, 5B:
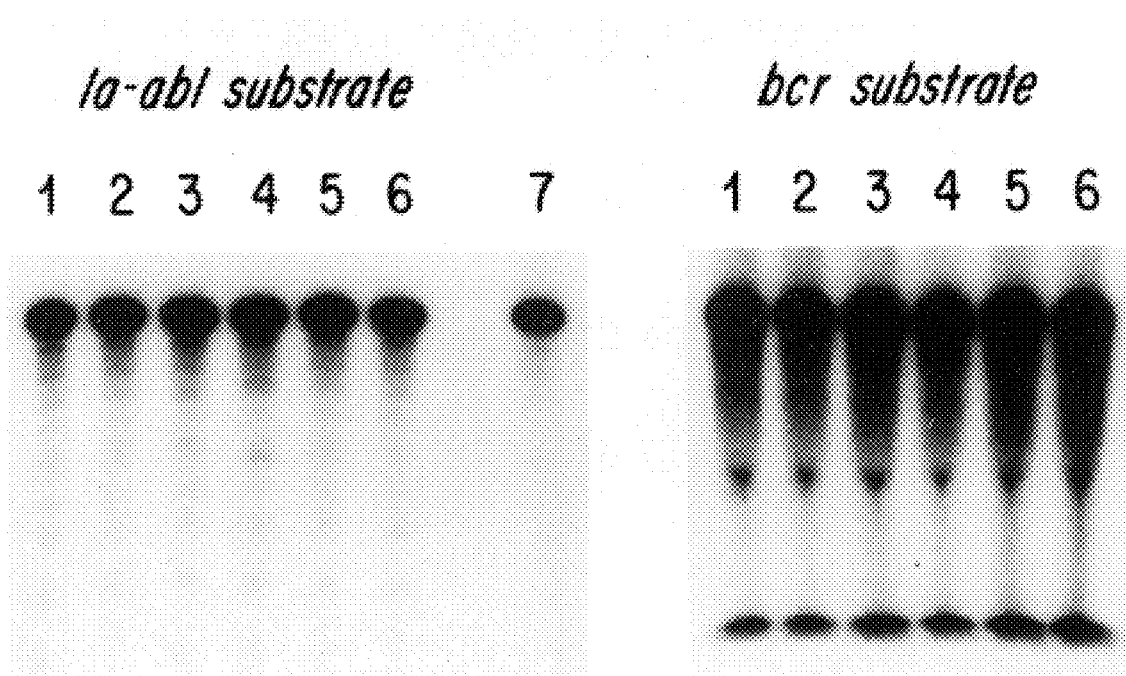
FIGS. 5 a and b depict the specificity of the ribozymes. Native abl and bcr substrates were not cleaved.

The specificity of the ribozymes for bcr-abl mRNA was tested by incubating the ribozymes with a synthetic normal abl substrate (FIG. 5a) or a synthetic normal bcr substrate (FIG. 5b). Ten pmol each of the ribozyme and a mixture of radiolabelled and non-radiolabelled substrate were incubated at 37° C. for 6 hours and subjected to denaturing gel electrophoresis on a 5% polyacrylamide gel. In FIG. 5a, Lanes 1–6 represent ribozymes L6(1)$_{31}$, L6(1)$_{21}$, L6(1)$_{11}$, L6(2)$_0$, L6(2)$_2$, and L6(2)$_3$, respectively. Lane 7 contained no ribozyme. In FIG. 5b, Lanes 1–5 were as described for FIG. 5a. Lane 6 contained no ribozyme. No cleavage products were detected in any of these reactions indicating that these ribozymes are all specific for bcr-abl mRNA. An anchor-minus L6(1) ribozyme (SEQ ID NO:23) also failed to cleave the normal abl substrate.

Cleavage of normal bcr was not anticipated as this molecule lacks the target cleavage site, however, this target site is present in the normal abl substrate. Failure of the ribozymes to cleave this molecule may have been due to the inability of the ribozymes to bind to the normal abl substrate or to the inability of the ribozymes to cleave the molecule once bound to it. In order to discriminate between these two possibilities, a substrate gel shift assay was performed.

Gel shift experiments were performed with either a radiolabelled L6 bcr-abl substrate or a radiolabelled normal abl substrate. Two predominant conformational species of the L6 bcr-abl RNA exist under the assay conditions. Both of these species are shifted by the L6(1) ribozymes. In contrast, the L6 (2)$_0$ and the L6(2)$_2$ ribozymes were only able to shift the faster migrating species of bcr-abl RNA. None of the ribozymes tested was able to shift the radiolabelled abl substrate which migrates as one conformational species on a native gel. This result indicates that the specificity of these ribozymes for the bcr-abl substrate was due to the inability of these ribozymes to bind to the normal abl substrate.

A kinetic analysis was performed to identify ribozymes with higher rates of reaction. The 21 nt and 11 nt-anchored ribozymes were initially chosen for further analysis because they exhibited specificity and the highest rates of cleavage at the early time points. This analysis would also enable us to determine the effect of anchor length on ribozyme activity.

Figure 7A:
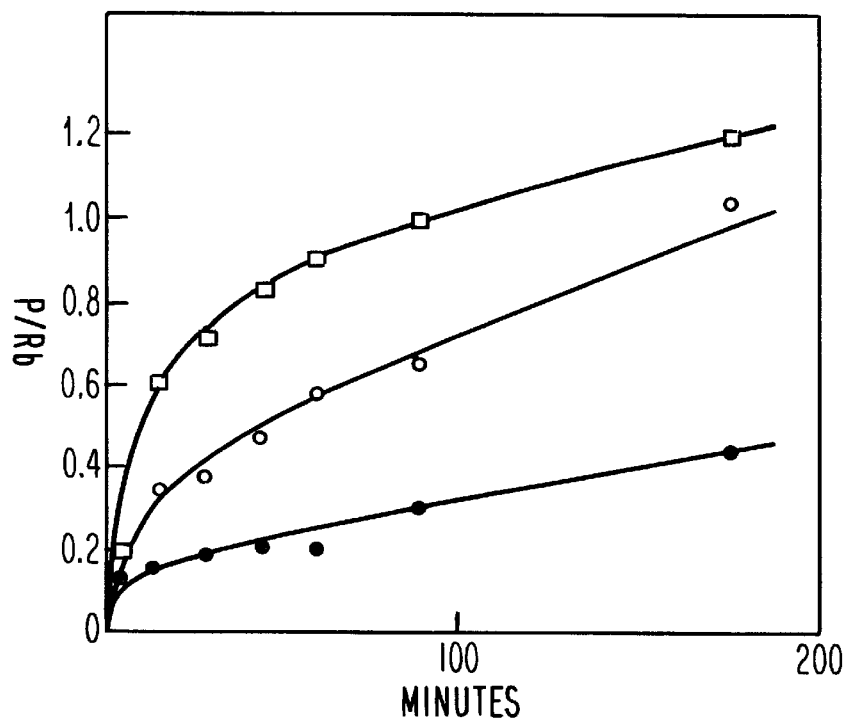
FIGS. 7 a–c depict the reaction kinetics for ribozymes L6(1)$_{11}$ and L6(1)$_{21}$.
Figure 7B:
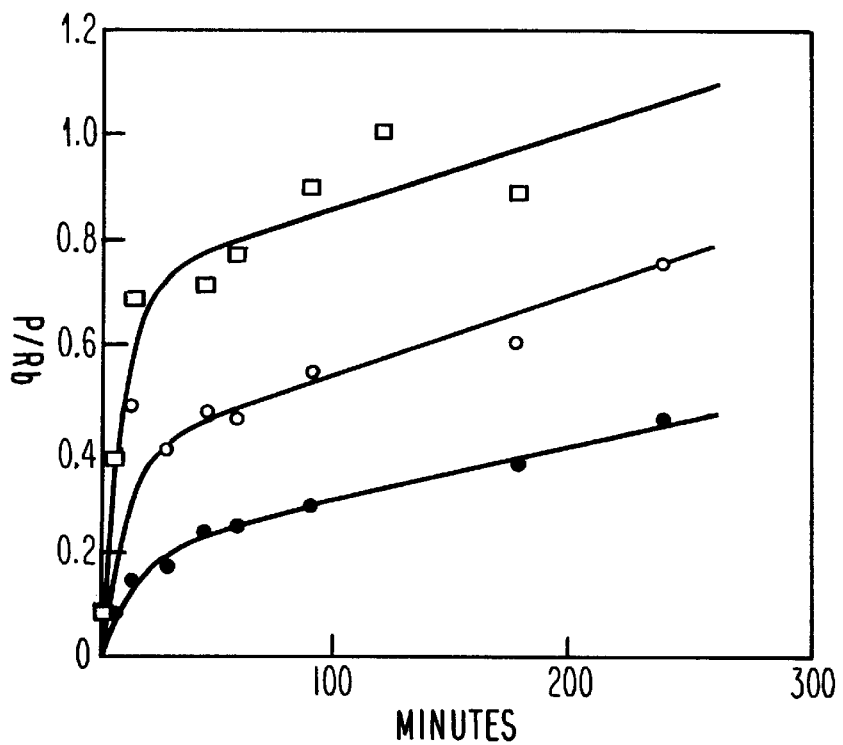
Figure 7C:
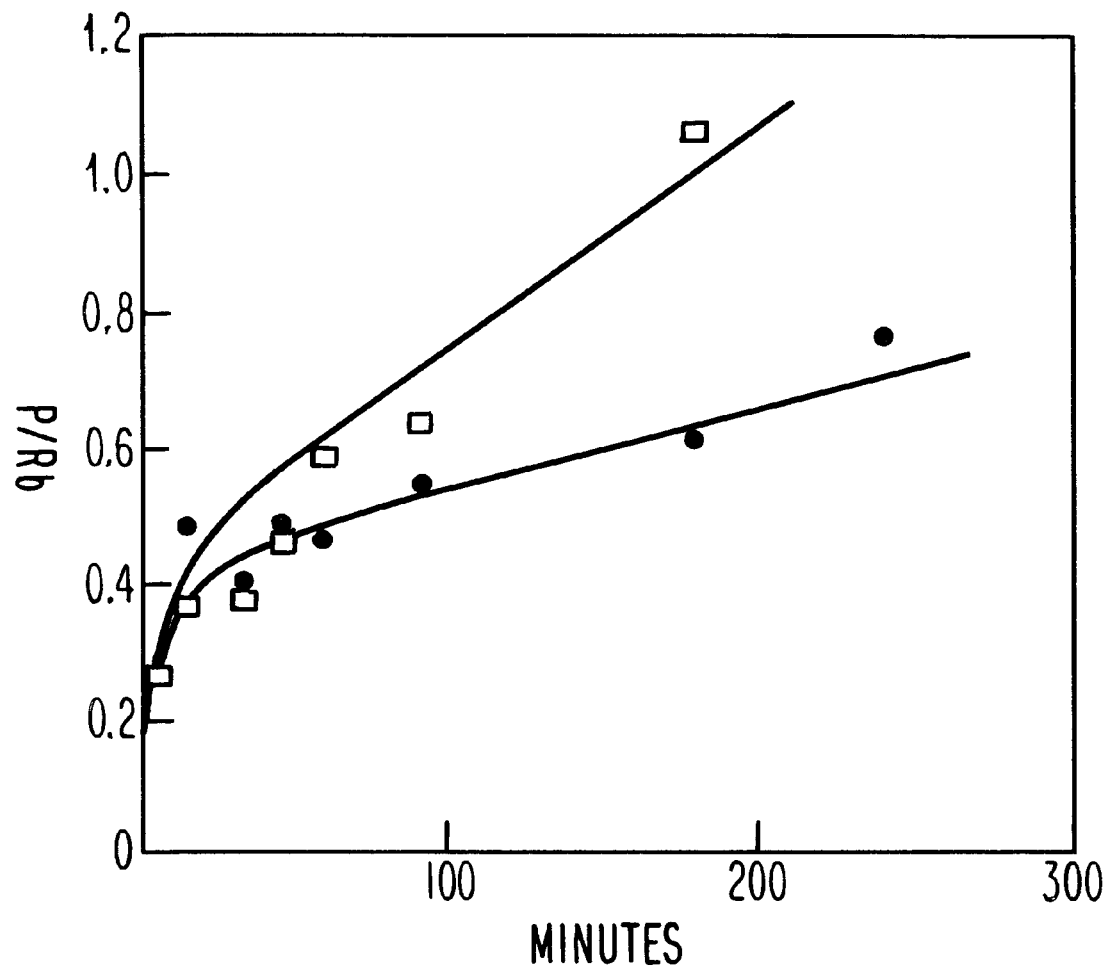

All experiments were carried out under conditions of substrate excess. Cleavage rates were determined for the 11 and 21 nt anchored ribozymes. FIG. 7a depicts the testing of L6(1)$_{11}$ at • 2:1; ○ 5:1; □ 10:1, substrate to ribozyme ratio. FIG. 7b depicts the testing of L6(1)$_{21}$ at the same substrate to ribozyme ratios as for L6(1)$_{11}$ above. FIG. 7c is a comparison of □ L6(1)$_{11}$ and • L6(1)$_{21}$ at a 5:1 ratio of substrate to ribozyme. Analysis of the results suggested that these reactions did not follow Michaelis-Menton kinetics (Haseloff, et al., Nature 1988, 334, 585–591). The data was therefore fitted to pseudo-first-order kinetics by plotting the ratio of the concentrations of product and ribozyme against time. Reaction rates were obtained from the linear regression of the reaction time course using the "Enzyfitter" program (Elsevier Biosoft).

Both ribozymes exhibited a burst of product formation at early time points followed by a much slower steady state rate. The slope of the initial burst indicates the catalytic rate to be 0.03/min for each ribozyme. The slope at later timepoints indicates the dissociation rates of the products from the ribozyme. Similar slopes were observed at the various ribozyme to substrate ratios for a given ribozyme. However, at all substrate to ribozyme ratios tested, the 21 nt anchored ribozyme exhibited a 3- to 4-fold slower turnover than the 11 nt ribozyme as indicated by the differences between the two slopes.

EXAMPLE 4

K28 - L6 Combination Treatment

Cells

K562 cells were obtained from the American Type Tissue Culture Collection and were passaged at a cell density of $10^5$/ml in a a modification MEM medium (JRH Biosciences) adjusted to 10% fetal bovine serum (Gibco-BRL) 1 mM sodium pyruvate (JRH Biosciences), 1×non-essential amino-acids (JRH Biosciences) and 2 mM glutamine (JRH Biosciences).

An 18-mer (SEQ ID NO: 7) 5'GAAGGGCTTTTGAACTCT 3' phosphorothioate antisense oligonucleotide spanning the K28 junction of the K28 fusion mRNA and an 18-mer (SEQ ID NO: 8) 5'TACGCGATTACGTTGAGT 3'phosphorothioate scrambled oligonucleotide of the same base composition as the K28 antisense oligonucleotide were purchased from Synthecell. An 18-mer (SEQ ID NO: 9) 5'GAAGGGCTTCTTCCTTAT 3'phosphodiester antisense oligonucleotide spanning the fusion of the L6 junction mRNA and an 18-mer (SEQ ID NO: 10) 5'TATTCCTTCTTCGGGAAG 3'phosphodiester oligonucleotide having the same base composition as the L6 antisense molecule in anti-parallel orientation were synthesized on a Milligen BioSearch 8750 DNA synthesizer, as a sianoethylphosphoroamidite synthesis (*Tetrahedron Lett.* 1981, 22, 1859–1862).

K562 cells were harvested for plating at 48 hours post passage, a time at which cells have been determined to be in exponential growth. Cells were pelleted, washed and resuspended in Opti-MEM (BRL-Gibco) at a cell density of $1\times10^6$/ml and plated in 96 well plates at a density of $5\times10^4$ cell/well.

One hundred µl of a mix containing 2 µg of lipofectin (BRL) and either 10 µg of a single oligonucleotide or 10 µg of each of two oligonucleotides in Opti-MEM were added per well. Untreated control cells received 100 µl Opti-MEM alone; the cells were incubated at 37° C. for 4 hours, at which time 50 µl of heat-inactivated 40% fetal bovine serum (Gibco-BRL) was added per well. Twenty hours post lipofection, 5 µg of the appropriate oligonucleotide or 5 µg of each two oligonucleotides in 25 µl of Opti-MEM were added to the designated wells.

At each time point, 20 µl of a 1:30 dilution of $^3$H-thymidine (6.7 ci/mMol) was added to each of the appropriate wells. The cells were incubated at 37° C. for 18 hours and then harvested and lysed on an automatic cell harvester (Skatron) according to manufacturers directions. DNA was collected on Skatron filtermats. The filters were dried, placed in scintillation vials with 3 mls ECO-Scint (National Diagnostics) and counted in a Beckman LS 9800 scintillation counter.

The effect of the K28 or combination K28/L6 antisense treatments on cell division was measured and compared to the effect obtained using a scrambled oligonucleotide having the same nucleotide content. A decrease in $^3$H-thymidine uptake by K562 cells treated with the L6-specific antisense was observed at 4 hours after the first antisense treatment (Table 1, Timepoint 1) and this trend was continued at all timepoints. A decrease in the $^3$H-thymidine incorporation by cells treated with a mixture of the K28 and L6 antisense compounds was also observed at all timepoints (Table 1). The magnitude of the effect varied at each timepoint, and the largest difference was observed at Timepoint 4. The combination treatment with the L-6 and K28 oligonucleotides resulted in a 1.6 to 3.9-fold reduction of $^3$H-thymidine uptake relative to that observed with the scrambled control (Table 1). Treatment with the L6 oligonucleotide alone resulted in a 3.1 to 4.8-fold reduction of $^3$H-thymidine uptake relative to that observed with the scrambled control (Table 1). Treatment with the K28 antisense alone resulted in only a slight reduction of $^3$H-thymidine uptake relative to control uptake at Timepoints 2 and 3 (Table 1). A comparison between the values obtained for the untreated control samples and any of the treated samples indicates that nonspecific toxicity occurred as a result of either lipofection or a combination of lipofection and oligonucleotide treatment.

The effect of antisense treatment on cellular morphology was also examined. The untreated and treated cells looked similar when examined at Timepoints 1 and 2. However, cells having large vacuoles that occupied the majority of the cellular volume were present in the samples treated with the L6 antisense alone and the L6/K28 combination at Timepoint 3. The percentage of cells having the vacuolar appearance was greatest at Timepoint 4 in each case. Cells having the vacuolar appearance were not observed in the untreated sample, in the sample treated with the K28 antisense oligonucleotide, or in the sample treated with any of the scrambled oligonucleotides. Therefore, there was a correlation between decreased $^3$H-thymidine uptake and the vacuolar morphology.

These results indicate that treatment of the K562 cell line with an L6-specific or a combination of the L6 and K28-specific antisense oligonucleotides decreased the growth rate of the K562 cell line. Treatment with the K28-specific oligonucleotide did not significantly decrease the growth rate of the K562 cell line, unlike the results reported in Szczylik et al., *Science* 1991, 253, 562–565, wherein decrease in leukemic colony formation was observed after treatment with a similar K28-specific antisense oligonucleotide having a phosphodiester backbone.

TABLE 1

| OLIGONUCLEOTIDE | TIMEPOINT | | | |
|---|---|---|---|---|
| | 1 | 2 | 3 | 4 |
| K28 | 179610 | 172220 | 120422 | 133225 |
| K28 scrambled | 180635 | 209980 | 141250 | 121580 |
| L6 | 51148 | 39136 | 10109 | 7923 |
| L6 scrambled | 244680 | 93215 | 39468 | 24887 |
| K28 + L6 | 99132 | 77300 | 35048 | 20156 |
| K28 + L6 scrambled | 158410 | 154240 | 108445 | 78045 |
| untreated | 261520 | 302410 | 439550 | 458780 |

Timepoint 1: Cells pulsed with $^3$H-thymidine at 4 hours post lipofection.
Timepoint 2: Cells pulsed with $^3$H-thymidine at 22 hours post lipofection.
Timepoint 3: Cells pulsed with $^3$H-thymidine at 28 hours post lipofection.
Timepoint 4: Cells pulsed with $^3$H-thymidine at 53 hours post lipofection.

The foregoing examples were meant to illustrate the invention and not to limit it in anyway. Those skilled in the art will recognize that modifications can be made which are within the spirit and scope of the invention as set forth in the appended claims.

What is claimed is:

1. A ribozyme which cleaves a substrate mRNA comprising:
    a catalytic sequence which cleaves a site of the substrate mRNA;
    two legs, one on each side of the catalytic sequence, wherein each of the legs hybridizes to a region of the substrate mRNA which is contiguous with the cleavage site;
    at least one anchor sequence complementary to the substrate mRNA at a location that is noncontiguous with the portions of the substrate mRNA complementary to the legs; and
    a spacer region which links one of the legs and the anchor sequence, wherein said spacer region permits cleavage of the substrate mRNA at a distance from the anchor sequence.

2. The ribozyme of claim 1 wherein the portion of the substrate mRNA that is complementary with the anchor sequence is located at least about 3 nucleotides away from the portions of the substrate mRNA that are complementary with the legs.

3. The ribozyme of claim 1 wherein the spacer region comprises nucleotides, or analogues thereof.

4. The ribozyme of claim 1 wherein the spacer region comprises a polyalkylene glycol.

5. The ribozyme of claim 1 wherein the spacer region comprises from about 1 to about 3000 nucleotide, or analogues thereof.

6. The ribozyme of claim 1 wherein the spacer region comprise a chemical spacer of a size equivalent to from about 1 to about 3000 nucleotides.

7. The ribozyme of claim 4 wherein the spacer region comprises at least about 13 nucleotides, or analogues thereof.

8. The ribozyme of claim 1 wherein each leg has at least about 4 nucleotides and the anchor region has at least about 2 nucleotides.

9. A ribozyme which cleaves an L6 mRNA having bcr exon 2 sequences fused at a junction to abl exon 2 sequences, said ribozyme comprising:
    a catalytic sequence which cleaves L6 mRNA;
    two legs, one on each side of the catalytic sequence, wherein each of the legs hybridizes to a region of the substrate mRNA which is contiguous with the cleavage site;
    at least one anchor sequence complementary to the substrate mRNA at a location that is noncontiguous with the portions of the substrate mRNA complementary to the legs; and
    a spacer region which links one of the legs and the anchor, wherein said spacer region permits cleavage of the L6 mRNA at a distance from the anchor sequence,
    wherein said ribozyme contains at least one region complementary to a bcr sequence of an L6 mRNA and at least one region complementary to an abl sequence of an L6 mRNA.

10. The ribozyme of claim 9 wherein said ribozyme also cleaves a K28 mRNA.

11. The ribozyme of claim 9 comprising the sequence GCCGCUGCUGAUGAGUCCGUGAGGAC-GAAAGGGCUUCUUCC (SEQ ID NO: 3).

12. The ribozyme of claim 9 wherein the catalytic sequence cleaves sequences in abl exon 2.

13. The ribozyme of claim 9 having at least 2 regions of complementarity to abl exon 2, at least one located 5' and at least one located 3' of the catalytic sequence.

14. The ribozyme of claim 9 wherein the catalytic sequence comprises the sequence CUGAUGAGUC-CGUGAGGACGAA (SEQ ID NO: 11).

15. The ribozyme of claim 14 wherein the ribozyme comprises a sequence: selected from the group consisting of

```
GUCAGAUGCCUGAUGAGUCCGUGAGGACGAAACUGGCAAGAACCCAAAAACUU,  (SEQ ID NO: 2)

CCUUAUUGAUGGUCAGCGGAAUGCUGUG,

GUCAGAUGCCUGAUGAGUCCGUGAGGACGAAACUGGCAAGAACCCAAAAACUU   (SEQ ID NO: 15)

CCUUAUUGAUGGUCAGCG,

GUCAGAUGCCUGAUGAGUCCGUGAGGACGAAACUGGCAAGAACCCAAAAACUU   (SEQ ID NO: 14)

CCUUAUUG,

GCCGCUGCUGAUGAGUCCGUGAGGACGAAAGGGCUUCUUCC,              (SEQ ID NO: 3)

and

GCCGCUGCUGAUGAGUCCGUGAGGACGAAAGGGCCACUUCC               (SEQ ID NO: 4)
```

16. The ribozyme of claim 15 wherein the region complementary to bcr exon 2 comprises from about 5 to about 31 nucleotides or analogues thereof.

17. The ribozyme of claim 16 wherein the region complementary to abl exon 2 comprises from about 10 to about 15 nucleotides or analogues thereof.

18. The ribozyme of claim 9 wherein the spacer region comprises at least about 13 nucleotides.

19. The ribozyme of claim 9 wherein the cleavage occurs at a CUU site.

20. The ribozyme of claim 9 wherein the cleavage occurs at a GUA site.

21. A ribozyme which cleaves an L6 mRNA having bcr exon 2 sequences fused at a junction to abl exon 2 sequences, wherein said ribozyme comprises:
   a catalytic sequence which cleaves a site within a fused bcr-abl junction on the L6 mRNA;
   two legs, wherein one of legs is located on either site of the catalytic sequence and each of the legs is complementary to an abl sequence on either side of the cleavage site;
   an anchor sequence which is complementary to sequences in bcr exon 2, wherein said anchor sequence is non-contiguous with said legs; and
   a spacer region which links the anchor sequence and a leg, wherein the spacer region permits cleavage of the L6 mRNA at a distance from the anchor sequence.

22. The ribozyme according to claim 21 wherein said cleavage site has the sequence CUU.

23. The ribozyme according to claim 21 wherein said cleavage site has the sequence GUA.

24. The ribozyme according to claim 21 wherein each leg comprises 4 to 15 nucleotides.

25. The ribozyme according to claim 21 wherein each leg comprises 7 nucleotides.

26. The ribozyme according to claim 21, wherein the anchor sequence comprises 2 to 500 nucleotides.

27. The ribozyme according to claim 26, wherein the anchor sequence comprises 5 to 100 nucleotides.

28. The ribozyme according to claim 21, wherein the ribozyme has a hammerhead motif.

29. The ribozyme according to claim 21, wherein the spacer region comprises about 13 nucleotides of sequence non-complementary to the L6 mRNA.

30. The ribozyme according to claim 9, wherein said ribozyme contains at least one region complementary to bcr exon 2.

31. The ribozyme according to claim 9 wherein said ribozyme contains at least one region complementary to abl exon 2.

* * * * *

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
      (A) LENGTH: 62

(B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 1:

CACAGCAUUC CGCUGACCAU CAAUAAGGAA GAAGCCCUUC AGCGGCCAGU AGCAUCUGAC    60

UU    62

(2) INFORMATION FOR SEQ ID NO: 2:

(i) SEQUENCE CHARACTERISTICS:
        (A) LENGTH: 81
        (B) TYPE: Nucleic Acid
        (C) STRANDEDNESS: Single
        (D) TOPOLOGY: Linear (iv) ANTI-SENSE:

(xi) SEQUENCE DESCRIPTION: SEQ ID NO: 2:

GUCAGAUGCC UGAUGAGUCC GUGAGGACGA AACUGGCAAG AACCCAAAAA CUUCCUUAUU    60

GAUGGUCAGC GGAAUGCUGU G    81

(2) INFORMATION FOR SEQ ID NO: 3:

(i) SEQUENCE CHARACTERISTICS:
        (A) LENGTH: 41
        (B) TYPE: Nucleic Acid
        (C) STRANDEDNESS: Single
        (D) TOPOLOGY: Linear (iv) ANTI-SENSE:

(xi) SEQUENCE DESCRIPTION: SEQ ID NO: 3:

GCCGCUGCUG AUGAGUCCGU GAGGACGAAA GGGCUUCUUC C    41

(2) INFORMATION FOR SEQ ID NO: 4:

(i) SEQUENCE CHARACTERISTICS:
        (A) LENGTH: 41
        (B) TYPE: Nucleic Acid
        (C) STRANDEDNESS: Single
        (D) TOPOLOGY: Linear (iv) ANTI-SENSE:

(xi) SEQUENCE DESCRIPTION: SEQ ID NO: 4:

GCCGCUGCUG AUGAGUCCGU GAGGACGAAA GGGCCACUUC C    41

(2) INFORMATION FOR SEQ ID NO: 5:

(i) SEQUENCE CHARACTERISTICS:
        (A) LENGTH: 41
        (B) TYPE: Nucleic Acid
        (C) STRANDEDNESS: Single
        (D) TOPOLOGY: Linear (iv) ANTI-SENSE:

(xi) SEQUENCE DESCRIPTION: SEQ ID NO: 5:

GCCGCUGCUG AUGAGUCCGU GAGGACGAAA GGGACACUUC C    41

(2) INFORMATION FOR SEQ ID NO: 6:

(i) SEQUENCE CHARACTERISTICS:
        (A) LENGTH: 41
        (B) TYPE: Nucleic Acid (C) STRANDEDNESS: Single
            (D) TOPOLOGY: Linear (iv) ANTI-SENSE:

(xi) SEQUENCE DESCRIPTION: SEQ ID NO: 6:

GCCGCUGCUG AUGAGUCCGU GAGGACGAAA GGAACACUUC C                              41

(2) INFORMATION FOR SEQ ID NO: 7:

(i) SEQUENCE CHARACTERISTICS:
            (A) LENGTH: 18
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 7:

GAAGGGCTTT TGAACTCT                                                       18

(2) INFORMATION FOR SEQ ID NO: 8:

(i) SEQUENCE CHARACTERISTICS:
            (A) LENGTH: 18
            (B) TYPE: Nucleic Acid
            (C) STRANDEDNESS: Single
            (D) TOPOLOGY: Linear (iv) ANTI-SENSE:

(xi) SEQUENCE DESCRIPTION: SEQ ID NO: 8:

TACGCGATTA CGTTGAGT                                                       18

(2) INFORMATION FOR SEQ ID NO: 9:

(i) SEQUENCE CHARACTERISTICS:
            (A) LENGTH: 18
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 9:

GAAGGGCTTC TTCCTTAT                                                       18

(2) INFORMATION FOR SEQ ID NO: 10:

(i) SEQUENCE CHARACTERISTICS:
            (A) LENGTH: 18
            (B) TYPE: Nucleic Acid
            (C) STRANDEDNESS: Single
            (D) TOPOLOGY: Linear (iv) ANTI-SENSE:

(xi) SEQUENCE DESCRIPTION: SEQ ID NO: 10:

TATTCCTTCT TCGGGAAG                                                       18

(2) INFORMATION FOR SEQ ID NO: 11:

(i) SEQUENCE CHARACTERISTICS:
            (A) LENGTH: 22
            (B) TYPE: Nucleic Acid
            (C) STRANDEDNESS: Single
            (D) TOPOLOGY: Linear (iv) ANTI-SENSE:

(xi) SEQUENCE DESCRIPTION: SEQ ID NO: 11:

CUGAUGAGUC CGUGAGGACG AA                                                    22

(2) INFORMATION FOR SEQ ID NO: 12:

(i) SEQUENCE CHARACTERISTICS:
            (A) LENGTH: 47
            (B) TYPE: Nucleic Acid
            (C) STRANDEDNESS: Single
            (D) TOPOLOGY: Linear (iv) ANTI-SENSE:

(xi) SEQUENCE DESCRIPTION: SEQ ID NO: 12:

TTCCATGGAG ACGCAGAAGC CCUUCAGCGG CCAGUAGCAU CUGACUU                         47

(2) INFORMATION FOR SEQ ID NO: 13:

(i) SEQUENCE CHARACTERISTICS:
            (A) LENGTH: 66
            (B) TYPE: Nucleic Acid
            (C) STRANDEDNESS: Single
            (D) TOPOLOGY: Linear (iv) ANTI-SENSE:

(xi) SEQUENCE DESCRIPTION: SEQ ID NO: 13:

GUCAGAUGCC UGAUGAGUCC GUGAGGACGA AACUGGCAAG AACCCAAAAA CTGCGTCTCC           60

ATGGAA                                                                      66

(2) INFORMATION FOR SEQ ID NO: 14:

(i) SEQUENCE CHARACTERISTICS:
            (A) LENGTH: 61
            (B) TYPE: Nucleic Acid
            (C) STRANDEDNESS: Single
            (D) TOPOLOGY: Linear (iv) ANTI-SENSE:

(xi) SEQUENCE DESCRIPTION: SEQ ID NO: 14:

GUCAGAUGCC UGAUGAGUCC GUGAGGACGA AACUGGCAAG AACCCAAAAA CUUCCUUAUU           60

G                                                                           61

(2) INFORMATION FOR SEQ ID NO: 15:

(i) SEQUENCE CHARACTERISTICS:
            (A) LENGTH: 71
            (B) TYPE: Nucleic Acid
            (C) STRANDEDNESS: Single
            (D) TOPOLOGY: Linear (iv) ANTI-SENSE:

(xi) SEQUENCE DESCRIPTION: SEQ ID NO: 15:

GUCAGAUGCC UGAUGAGUCC GUGAGGACGA AACUGGCAAG AACCCAAAAA CUUCCUUAUU           60

GAUGGUCAGC G                                                                71

(2) INFORMATION FOR SEQ ID NO: 16:

(i) SEQUENCE CHARACTERISTICS:
            (A) LENGTH: 40
            (B) TYPE: Nucleic Acid
            (C) STRANDEDNESS: Single
            (D) TOPOLOGY: Linear (iv) ANTI-SENSE:

(xi) SEQUENCE DESCRIPTION: SEQ ID NO: 16:

ATTGCGATAG GATTGAATTC AACTCGTGTG TGAAACTCCA                    40

(2) INFORMATION FOR SEQ ID NO: 17:

(i) SEQUENCE CHARACTERISTICS:
            (A) LENGTH: 40
            (B) TYPE: Nucleic Acid
            (C) STRANDEDNESS: Single
            (D) TOPOLOGY: Linear (iv) ANTI-SENSE:

(xi) SEQUENCE DESCRIPTION: SEQ ID NO: 17:

AATGCGATAG GATTGAATTC GTCCAGCGAG AAGGTTTTCC                    40

(2) INFORMATION FOR SEQ ID NO: 18:

(i) SEQUENCE CHARACTERISTICS:
            (A) LENGTH: 67
            (B) TYPE: Nucleic Acid
            (C) STRANDEDNESS: Single
            (D) TOPOLOGY: Linear (iv) ANTI-SENSE:

(xi) SEQUENCE DESCRIPTION: SEQ ID NO: 18:

ATTGCGATAG GATTGAATTC AAGCTTAAGT GTTTCAGAAG CTTCTCCCTG ACATCCGTGG    60

AGCTGCA                                                              67

(2) INFORMATION FOR SEQ ID NO: 19:

(i) SEQUENCE CHARACTERISTICS:
            (A) LENGTH: 61
            (B) TYPE: Nucleic Acid
            (C) STRANDEDNESS: Single
            (D) TOPOLOGY: Linear (iv) ANTI-SENSE:

(xi) SEQUENCE DESCRIPTION: SEQ ID NO: 19:

AATGCGATAG GATTGAATTC CGGAGACTCA TCATCTTCCT TATTGATGGT CAGCGGAATG    60

C                                                                    61

(2) INFORMATION FOR SEQ ID NO: 20:

(i) SEQUENCE CHARACTERISTICS:
            (A) LENGTH: 23
            (B) TYPE: Nucleic Acid
            (C) STRANDEDNESS: Single
            (D) TOPOLOGY: Linear (iv) ANTI-SENSE:

(xi) SEQUENCE DESCRIPTION: SEQ ID NO: 20:

TAGGACTGCT CTCACTTCTC ACG                                     23

(2) INFORMATION FOR SEQ ID NO: 21:

(i) SEQUENCE CHARACTERISTICS:
            (A) LENGTH: 24
            (B) TYPE: Nucleic Acid
            (C) STRANDEDNESS: Single
            (D) TOPOLOGY: Linear (iv) ANTI-SENSE:

(xi) SEQUENCE DESCRIPTION: SEQ ID NO: 21:

ATCTGCCTGA AGCTGGTGGG CTGC                24

(2) INFORMATION FOR SEQ ID NO: 22:

(i) SEQUENCE CHARACTERISTICS:
        (A) LENGTH: 23
        (B) TYPE: Nucleic Acid
        (C) STRANDEDNESS: Single
        (D) TOPOLOGY: Linear (iv) ANTI-SENSE:

(xi) SEQUENCE DESCRIPTION: SEQ ID NO: 22:

ATGCTTAGAG TGTTATCTCC ACT                 23

(2) INFORMATION FOR SEQ ID NO: 23:

(i) SEQUENCE CHARACTERISTICS:
        (A) LENGTH: 50
        (B) TYPE: Nucleic Acid
        (C) STRANDEDNESS: Single
        (D) TOPOLOGY: Linear (iv) ANTI-SENSE:

(xi) SEQUENCE DESCRIPTION: SEQ ID NO: 23:

GUCAGAUGCC UGAUGAGUCC GUGAGGACGA AACUGGCAAG AACCCAAAAA   50